US011767351B2

(12) United States Patent
Kalkum et al.

(10) Patent No.: US 11,767,351 B2
(45) Date of Patent: Sep. 26, 2023

(54) RECOMBINANT LECTIN AND USES THEREOF

(71) Applicant: CITY OF HOPE, Duarte, CA (US)

(72) Inventors: Markus Kalkum, Azusa, CA (US); Yoko Fujita-Yamaguchi, Pasadena, CA (US); Karine Bagramyan, North Hollywood, CA (US); Teresa B. Hong, El Monte, CA (US); Sarah Shuck, Orange, CA (US)

(73) Assignee: CITY OF HOPE, Duarte, CA (US)

( * ) Notice: Subject to any disclaimer, the term of this patent is extended or adjusted under 35 U.S.C. 154(b) by 3 days.

(21) Appl. No.: 17/394,313

(22) Filed: Aug. 4, 2021

(65) Prior Publication Data

US 2021/0395315 A1 Dec. 23, 2021

Related U.S. Application Data

(62) Division of application No. 16/165,725, filed on Oct. 19, 2018, now abandoned.

(60) Provisional application No. 62/574,626, filed on Oct. 19, 2017, provisional application No. 62/574,636, filed on Oct. 19, 2017.

(51) Int. Cl.

| | |
|---|---|
| ***G01N 33/574*** | (2006.01) |
| ***C07K 14/36*** | (2006.01) |
| ***G01N 33/58*** | (2006.01) |
| ***A61K 51/08*** | (2006.01) |

(52) U.S. Cl.

CPC .............. *C07K 14/36* (2013.01); *A61K 51/08* (2013.01); *G01N 33/57419* (2013.01); *G01N 33/57438* (2013.01); *G01N 33/57492* (2013.01); *G01N 33/582* (2013.01); *C07K 2319/60* (2013.01)

(58) Field of Classification Search

None

See application file for complete search history.

(56) References Cited

FOREIGN PATENT DOCUMENTS

WO 2016/178996 A1 11/2016

OTHER PUBLICATIONS

Carpentier, G., "Protein Array Analyzer for ImageJ," ImageJ News 10, presented at the poster session at the ImageJ Userand Developer Conference, Oct. 27-29, 2010.
Chen, K., et al., "Design and Development of Molecular Imaging Probes," Curr. Top. Med. Chem. 10(12):1227-1236 (2010).
Cheng, H. N., et al., "Solution NMR Spectroscopy of Food Polysaccharides," Polymer Reviews 52(2):81-114 (2012).
Chothia, C., et al., "The Relation Between the Divergence of Sequence and Structure in Proteins," EMBO J. 5(4):823-826 (1986).
Dube, D. H., et al., "Glycans in Cancer and Inflammation—Potential for Therapeutics and Diagnostics," Nat. Rev. Drug Discov. 4:477-488 (2005).
Fishbach, et al., Annotation of *Streptomyces* sp. Mg1; submitted (Feb. 2008) to the EMBL/GenBank/DDBJ database. Accession No. B4VFE2.
Fujimoto, Z., et al., "The Structure of a Streptomyces Avermitilis α-L-Rhamnosidase Reveals a Novel Carbohydrate-Binding Module CBM67 Within the Six-Domain Arrangement," J. Biol. Chem. 288(17):12376-12385 (2013).
Fujita, Y., et al., "Hemaggutination by Culture Broth of Actinomycetes and Aspergillus," J. Gen. Appl. Microbiol. 18:73-75 (1972).
Fujita, Y., et al., "Sugar Specificity of Anti-B Hemagglutinin Produced by *Streptomyces* sp," Biochem. Biophys. Res. Comm. 53(2):495-501 (1973).
Fujita, Y., et al., "Purification and Properties of an Anti-B Hemagglutinin Produced by *Streptomyces* sp," Biochemistry 14:4465-4470 (1975).
Fujita-Yamaguchi, Y., et al., "Studies on Carbohydrate Binding to a Lectin Purified from *Streptomyces* sp," Biochim. Biophys. Acta 701:86-92 (1982).
Greenspan, N. S., et al., "Defining Epitopes: It's Not as Easy as It Seems," Nat. Biotechnol. 17:936-937 (1999).
Guerrero, F., et al., "Tandem SUMO Fusion Vectors for Improving Soluble Protein Expression and Purification," Protein Expression and Purification 116:42-49 (2015).
Harrison, J., et al., "Recently Published Streptomyces Genome Sequences," Microbiol. Biotechnol. 7(5):373-380 (2014).
Hoefler, B. C., et al., "De Novo Assembly of the *Streptomyces* sp. Strain Mg1 Genome Using PacBio Single-Molecule Sequencing," Genome Announcements 1(4):e00535-13 (2013).
Hosono, M., et al., "Tandem Repeat Structure of Rhamnose-Binding Lectin from Catfish (*Silurus asotus*) Eggs," Biochim. Biophys. Acta 1472:668-675 (1999).
Lamoth, F., "Galactomannan and 1,3-β-D-Glucan Testing for the Diagnosis of Invasive Aspergillosis," J. Fungi 2(22):1-8 (2016).
Mikayama, T., et al., "Molecular Cloning and Functional Expression of a cDNA Encoding Glycosylation-Inhibiting Factor," Proc. Natl. Acad. Sci. USA 90:10056-10060 (1993).
Misto, M.Y., et al., "Bacterial Glycobiology: Rhamnose-Containing Cell Wall Polysaccharides in Gram-Positive Bacteria," FEMS Microbiol. Rev. 40:464-479 (2016).

(Continued)

*Primary Examiner* — Jennifer E Graser
(74) *Attorney, Agent, or Firm* — Perkins Coie LLP; Lara J. Dueppen; Allison M. Glasunow

(57) ABSTRACT

Disclosed herein are a recombinant *Streptomyces* S27S5 hemagglutinin (SHA), and homologues thereof, and a fusion protein of a fluorescent protein (such as GFP and mCherry1) and SHA or a homologue thereof, which specifically bind to carbohydrates, including oligomeric sugars that terminate in L-rhamnose or D-galactose. The SHA, SHA homologues, and fusion proteins can be used to detect a variety of microorganisms or cancer or tumor antigens.

6 Claims, 17 Drawing Sheets
(16 of 17 Drawing Sheet(s) Filed in Color)
Specification includes a Sequence Listing.

(56) References Cited

OTHER PUBLICATIONS

Negre-Salvayre, A., et al., "Hyperglycemia and Glycation in Diabetic Complications," Antioxidants & Redox Signaling 11(12):3071-3109 (2009).
Ng, S. K., et al., "A Recombinant Horseshoe Crab Plasma Lectin Recognizes Specific Pathogen-Associated Molecular Patterns of Bacteria Through Rhamnose," PLoS ONE 9(12):e115296 (2014).
Nolling, J., et al., "Genome Sequence and Comparative Analysis of the Solvent-Producing Bacterium Clostridium Acetobutylicum," J.Bacteriol. 183(16):4823-4838 (2001).
Noorani, et al. Submitted (Jul. 2015) to the EMBL/GenBank/DDBJ databases. Accession No. A0A0M8SFT9; uncharacterized protein Streptomyces.
Ogawa, T., et al., "Diversified Carbohydrate-Binding Lectins from Marine Resources," J. Amino Acids, 20 pages, doi:10.4061/2011/838914 (2011).
Ozeki, Y., et al., "Developmental Expression of D-Galactoside-Binding Lectin in Sea Urchin (*Anthocidaris crassispina*) Eggs," Exp. Cell Res. 216:318-324 (1995).
Rudinger, J., et al., "Characteristics of the Amino Acids as Components of a Peptide Hormone Sequence," Peptide Hormones, Biol. Counsel pp. 5-7 (1976).
Sharon, N., "Bacterial Lectins, Cell-Cell Recognition and Infectious Disease," FEBS Letters 217:145-157 (1987).
Smith, S. V., et al., "Production and Selection of Metal PET Radioisotopes for Molecular Imaging," Radioisotopes—Applications in Bio-Medical Science, Prof. Nirmal Singh (Ed.), ISBN: 978-953-307-748-2 (2011).
Sullivan, L., et al., "Analysis of the Clostridial Hydrophobic with a Conserved Tryptophan Family (ChW) of Proteins in *Clostridium Acetobutylicum* with Emphasis on ChW14 and ChW16/17," Enzyme Microbial Technol. 42:29-43 (2007).
Tateno, H., et al., "Rhamnose-Binding Lectins from Steelhead Trout (*Oncorhynchus mykiss*) Eggs Recognize Bacterial Lipopolysaccharides and Lipoteichoic Acid," Biosci. Biotechnol. Biochem. 66(3):604-612 (2002).
Tateno, H., "SUEL-Related Lectins, a Lectin Family Wdely Distributed Throughout Organisms," Biosci. Biotechnol. Biochem. 74(6):1141-1144 (2010).
Tateno, H., et al., "Distribution and Molecular Evolution of Rhamnose-Binding Lectins in *Salmonidae*: Isolation and Characterization of Two Lectins from White-Spotted Charr (*Salvelinus leucomaenis*) Eggs," Biosci. Biotechol. Biochem.66(6):1356-1365 (2002).
Tateno, H., et al., "Isolation and Characterization of Rhamnose-binding Lectins from Eggs of Steelhead Trout (*Oncorhynchus mykiss*) Homologous to Low Density Lipoprotein Receptor Superfamily," J. Biol. Chem. 273(30):19190-19197 (1998).
Terada, T., et al., "Structural Characterization of a Rhamnose-Binding Glycoprotein (Lectin) from Spanish Mackerel (*Scornberomorous niphonius*) Eggs," Biochim. Biophys. Acta 1770:617-629 (2007).
Theodoratou, E., et al., "The Role of Glycosylation in IBD," Nat. Rev. Gastroenterol. Hepatol. 11:588-600 (2014).
Ueno, T., et al., "Fluorescent Probes for Sensing and Imaging," Nat. Meth.8(8):642-645 (2011).
Van Der Beek, S. L., et al., "GacA is Essential for Group A *Streptococcus* and Defines a New Class of Monomeric dTDP-4-Dehydrorhamnose Reductases (RmlD)," Mol. Microbiol. 98(5):946-962 (2015).
Van Zyl, W. F., et al., "Use of the mCherry Fluorescent Protein to Study Intestinal Colonization by *Enterococcus Mundtii* ST4SA and *Lactobacillus Plantarum* 423 in Mice," Appl. Environ. Microbio 81(17):5993-6002 (2015).
Watanabe, Y., et al., "The Function of Rhamnose-Binding Lectin in Innate Immunity by Restricted Binding to Gb3," Devel. Comp. Immunol. 33:187-197 (2009).
Wood, W. I., "Gene Cloning Based on Long Oligonucleotide Probes," Guide to Molecular Cloning Techniques vol. 152, Section IX, Ch. 49, pp. 443-457 (1987).
Yan, X., et al., "Strain Prioritization and Genome Mining for Enediyne Natural Products," MBio. 7(6):e02104-e02116 (2016).
Yasuda, E., et al., "Lectin Microarray Reveals Binding Profiles of Lactobacillus Casei Strains in a Comprehensive Analysis of Bacterial Cell Wall Polysaccharides," Applied Environmental Microbiol. 77(13):4539-4546 (2011).
Zhang, Q., et al., "A Perspective on the Maillard Reaction and the Analysis of Protein Glycation by Mass Spectrometry: Probing the Pathogenesis of Chronic Disease," J. Proteome Res. 8(2):754-769 (2009).

| Array # | Glycan |
|---|---|
| 2 | β-Gal-Sp |
| 5 | α-Rha-Sp |
| 10 | Gal-α-1,3-Gal-β-1,3-GlcNAc-β-Sp |
| 17 | Gal-α-1,3-Gal-β-1,4-Glc-β-Sp |
| 18 | Gal-α-1,4-Gal-β-1,4-Glc-β-Sp |
| 20 | GalNAc-β-1,3-Gal-β-1,4-Glc-β-Sp |
| 36 | Gal-α-1,4-Gal-β-1,3-GlcNAc-β-Sp |
| 59 | Gal-α-1,3-(Fuc-α-1,2)-Gal-β- [Blood B antigen trisaccharide]-Sp1 |
| 62 | Gal-α-1,3-(Fuc-α-1,2)-Gal-β-1,4-Glc-β- [Blood B antigen tetrasaccharide]-Sp1 |
| 74 | Gal-α-1,4-Gal-β-1,4-GlcNAc-β-Sp1 |
| 88 | Gal-α-1,3-Gal-β-Sp1 |

| | SHA Domain # | | number of residues |
|---|---|---|---|
| SEQ ID NO:44 | 1 | AHV-EGIGWQGAVC--DG---AVAGTTGQSRRMEA | 29 |
| SEQ ID NO:45 | 2 | AHLAD-IGWQGWACAADG-KAVTVGTTGQSRRMEA | 33 |
| SEQ ID NO:46 | 3 | AHVAD-YGWLN----AEGGNPVYVGTTGQSRRMEA | 30 |

5 10 15 20 25 30 35

$^{68}$Ga-DOTA-GFP-scFv (non-specific control)

$^{68}$Ga-DOTA-GFP-SHA

SEQUENCE LISTING

```
<160> NUMBER OF SEQ ID NOS: 46

<210> SEQ ID NO 1
<211> LENGTH: 60
<212> TYPE: DNA
<213> ORGANISM: Artificial Sequence
<220> FEATURE:
<223> OTHER INFORMATION: P1f primer

<400> SEQUENCE: 1

tgcgcgaacg cgcacctggc ggacatcggt tggcagggtt gggcgtgcgc ggcggacggt      60


<210> SEQ ID NO 2
<211> LENGTH: 60
<212> TYPE: DNA
<213> ORGANISM: Artificial Sequence
<220> FEATURE:
<223> OTHER INFORMATION: P2f primer

<400> SEQUENCE: 2

cgtatggaag cggcggttat cgcgacctct ggtaccggtg gtgtttgcgc gaacgcgcac      60


<210> SEQ ID NO 3
<211> LENGTH: 60
<212> TYPE: DNA
<213> ORGANISM: Artificial Sequence
<220> FEATURE:
<223> OTHER INFORMATION: P3f primer

<400> SEQUENCE: 3

gtttgcgacg gtgcggttgc gggtaccacc ggtcagtctc gtcgtatgga agcggcggtt      60
```

-continued

<210> SEQ ID NO 4
<211> LENGTH: 60
<212> TYPE: DNA
<213> ORGANISM: Artificial Sequence
<220> FEATURE:
<223> OTHER INFORMATION: P4f primer

<400> SEQUENCE: 4
gcggcgcacg ttgaaggtat cggttggcag ggtgcggttt gcgacggtgc ggttgcgggt 60

<210> SEQ ID NO 5
<211> LENGTH: 60
<212> TYPE: DNA
<213> ORGANISM: Artificial Sequence
<220> FEATURE:
<223> OTHER INFORMATION: 5af primer

<400> SEQUENCE: 5
aaagaattcg cgccggcggc gcgtaccgtt tgctacgcgg cgcacgttga aggtatcggt 60

<210> SEQ ID NO 6
<211> LENGTH: 60
<212> TYPE: DNA
<213> ORGANISM: Artificial Sequence
<220> FEATURE:
<223> OTHER INFORMATION: P1r primer

<400> SEQUENCE: 6
tccatacgac gagactgacc ggtggtacca acggtaaccg ctttaccgtc cgccgcgcac 60

<210> SEQ ID NO 7
<211> LENGTH: 60
<212> TYPE: DNA
<213> ORGANISM: Artificial Sequence
<220> FEATURE:
<223> OTHER INFORMATION: P2r primer

<400> SEQUENCE: 7
gcctgcgccg caacagaacc gttaccaact tgcagaccca gcgcttccat acgacgagac 60

<210> SEQ ID NO 8
<211> LENGTH: 60
<212> TYPE: DNA
<213> ORGANISM: Artificial Sequence
<220> FEATURE:
<223> OTHER INFORMATION: P3r primer

<400> SEQUENCE: 8
ttaccacccg ccgcgttcag ccaaccgtag tccgcaacgt gcgcctgcgc cgcaacagaa 60

<210> SEQ ID NO 9
<211> LENGTH: 60
<212> TYPE: DNA
<213> ORGANISM: Artificial Sequence
<220> FEATURE:
<223> OTHER INFORMATION: P4ar primer

<400> SEQUENCE: 9
cgacgggact gaccagtagt gccaacgtaa accgggttgc cacccgccgc gttcagccaa 60

<210> SEQ ID NO 10
<211> LENGTH: 60
<212> TYPE: DNA
<213> ORGANISM: Artificial Sequence
<220> FEATURE:

<223> OTHER INFORMATION: P5ar primer

<400> SEQUENCE: 10
tttctcgagt taaacccaga tacgaaccgc ttccatacga cgggactgac cagtagtgcc 60

<210> SEQ ID NO 11
<211> LENGTH: 48
<212> TYPE: DNA
<213> ORGANISM: Artificial Sequence
<220> FEATURE:
<223> OTHER INFORMATION: PDSLA108Ef primer

<400> SEQUENCE: 11
gactacggtt ggctgaacgc ggaaggtggc aacccggttt acgttggc 48

<210> SEQ ID NO 12
<211> LENGTH: 48
<212> TYPE: DNA
<213> ORGANISM: Artificial Sequence
<220> FEATURE:
<223> OTHER INFORMATION: PDSLA108Er primer

<400> SEQUENCE: 12
gccaacgtaa accgggttgc caccttccgc gttcagccaa ccgtagtc 48

<210> SEQ ID NO 13
<211> LENGTH: 10
<212> TYPE: PRT
<213> ORGANISM: Artificial Sequence
<220> FEATURE:
<223> OTHER INFORMATION: N-terminal amino acid
<220> FEATURE:
<221> NAME/KEY: MISC_FEATURE
<222> LOCATION: (2)..(2)
<223> OTHER INFORMATION: X is an undetermined residue
<220> FEATURE:
<221> NAME/KEY: MISC_FEATURE
<222> LOCATION: (9)..(9)
<223> OTHER INFORMATION: X is an undetermined residue

<400> SEQUENCE: 13

Ala Xaa Thr Val Cys Tyr Ala Ala Xaa Val
1 5 10

<210> SEQ ID NO 14
<211> LENGTH: 33
<212> TYPE: PRT
<213> ORGANISM: Artificial Sequence
<220> FEATURE:
<223> OTHER INFORMATION: N-terminal amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 14

Ala Arg Thr Val Cys Tyr Ala Ala His Val Glu Gly Ile Gly Trp Gln
1 5 10 15

Gly Ala Val Cys Asp Gly Ala Val Ala Xaa Thr Thr Xaa Gln Ser Arg
20 25 30

Arg

<210> SEQ ID NO 15

-continued

<211> LENGTH: 6
<212> TYPE: PRT
<213> ORGANISM: Artificial Sequence
<220> FEATURE:
<223> OTHER INFORMATION: N-terminal sequence of SHA

<400> SEQUENCE: 15

Ala Arg Thr Val Cys Tyr
1 5

<210> SEQ ID NO 16
<211> LENGTH: 7
<212> TYPE: PRT
<213> ORGANISM: Artificial Sequence
<220> FEATURE:
<223> OTHER INFORMATION: homologous SHA domain

<400> SEQUENCE: 16

Ala Arg Thr Val Cys Tyr Ala
1 5

<210> SEQ ID NO 17
<211> LENGTH: 29
<212> TYPE: PRT
<213> ORGANISM: Artificial Sequence
<220> FEATURE:
<223> OTHER INFORMATION: SHA domain 1

<400> SEQUENCE: 17

Ala His Val Glu Gly Ile Gly Trp Gln Gly Ala Val Cys Asp Gly Ala
1 5 10 15

Val Ala Gly Thr Thr Gly Gln Ser Arg Arg Met Glu Ala
20 25

<210> SEQ ID NO 18
<211> LENGTH: 14
<212> TYPE: PRT
<213> ORGANISM: Artificial Sequence
<220> FEATURE:
<223> OTHER INFORMATION: homologous SHA domain

<400> SEQUENCE: 18

Ala Val Ile Ala Thr Ser Gly Thr Gly Gly Val Cys Ala Asn
1 5 10

<210> SEQ ID NO 19
<211> LENGTH: 33
<212> TYPE: PRT
<213> ORGANISM: Artificial Sequence
<220> FEATURE:
<223> OTHER INFORMATION: SHA domain 2

<400> SEQUENCE: 19

Ala His Leu Ala Asp Ile Gly Trp Gln Gly Trp Ala Cys Ala Ala Asp
1 5 10 15

Gly Lys Ala Val Thr Val Gly Thr Thr Gly Gln Ser Arg Arg Met Glu
20 25 30

Ala

<210> SEQ ID NO 20
<211> LENGTH: 13
<212> TYPE: PRT
<213> ORGANISM: Artificial Sequence
<220> FEATURE:
<223> OTHER INFORMATION: homologous SHA domain

<400> SEQUENCE: 20

Leu Gly Leu Gln Val Gly Asn Gly Ser Val Ala Ala Gln
1 5 10

<210> SEQ ID NO 21
<211> LENGTH: 30
<212> TYPE: PRT
<213> ORGANISM: Artificial Sequence
<220> FEATURE:
<223> OTHER INFORMATION: SHA domain 3

<400> SEQUENCE: 21

Ala His Val Ala Asp Tyr Gly Trp Leu Asn Ala Glu Gly Gly Asn Pro
1 5 10 15

Val Tyr Val Gly Thr Thr Gly Gln Ser Arg Arg Met Glu Ala
20 25 30

<210> SEQ ID NO 22
<211> LENGTH: 5
<212> TYPE: PRT
<213> ORGANISM: Artificial Sequence
<220> FEATURE:
<223> OTHER INFORMATION: homologous SHA domain

<400> SEQUENCE: 22

Val Arg Ile Trp Val
1 5

<210> SEQ ID NO 23
<211> LENGTH: 38
<212> TYPE: PRT
<213> ORGANISM: Artificial Sequence
<220> FEATURE:
<223> OTHER INFORMATION: ChW domain

<400> SEQUENCE: 23

Ala His Val Gln Asn Ile Gly Trp Gln Asp Trp Val Ser Asn Gly Ala
1 5 10 15

Glu Ala Gly Thr Asp Gly Lys Gly Leu Arg Val Glu Ala Leu Arg Ile
20 25 30

Lys Leu Glu Asn Met Pro
35

<210> SEQ ID NO 24
<211> LENGTH: 11
<212> TYPE: PRT
<213> ORGANISM: Artificial Sequence
<220> FEATURE:
<223> OTHER INFORMATION: SHA domain

<400> SEQUENCE: 24

Gly Thr Thr Gly Gln Ser Arg Arg Met Glu Ala
1 5 10

<210> SEQ ID NO 25
<211> LENGTH: 131
<212> TYPE: PRT
<213> ORGANISM: Artificial Sequence
<220> FEATURE:
<223> OTHER INFORMATION: recombinant SHA

<400> SEQUENCE: 25

Ala Arg Thr Val Cys Tyr Ala Ala His Val Glu Gly Ile Gly Trp Gln
1 5 10 15

-continued

```
Gly Ala Val Cys Asp Gly Ala Val Ala Gly Thr Thr Gly Gln Ser Arg
            20                  25                  30

Arg Met Glu Ala Ala Val Ile Ala Thr Ser Gly Thr Gly Gly Val Cys
        35                  40                  45

Ala Asn Ala His Leu Ala Asp Ile Gly Trp Gln Gly Trp Ala Cys Ala
    50                  55                  60

Ala Asp Gly Lys Ala Val Thr Val Gly Thr Thr Gly Gln Ser Arg Arg
65                  70                  75                  80

Met Glu Ala Leu Gly Leu Gln Val Gly Asn Gly Ser Val Ala Ala Gln
                85                  90                  95

Ala His Val Ala Asp Tyr Gly Trp Leu Asn Ala Glu Gly Gly Asn Pro
            100                 105                 110

Val Tyr Val Gly Thr Thr Gly Gln Ser Arg Arg Met Glu Ala Val Arg
        115                 120                 125

Ile Trp Val
    130
```

<210> SEQ ID NO 26
<211> LENGTH: 1155
<212> TYPE: DNA
<213> ORGANISM: Artificial Sequence
<220> FEATURE:
<223> OTHER INFORMATION: mCherry1-acidic-linker-SHA
<220> FEATURE:
<221> NAME/KEY: misc_feature
<222> LOCATION: (1)..(708)
<223> OTHER INFORMATION: mCherry1
<220> FEATURE:
<221> NAME/KEY: misc_feature
<222> LOCATION: (709)..(735)
<223> OTHER INFORMATION: acidic linker
<220> FEATURE:
<221> NAME/KEY: misc_feature
<222> LOCATION: (736)..(1128)
<223> OTHER INFORMATION: SHA bases
<220> FEATURE:
<221> NAME/KEY: misc_feature
<222> LOCATION: (1129)..(1134)
<223> OTHER INFORMATION: XhoI cloning site
<220> FEATURE:
<221> NAME/KEY: misc_feature
<222> LOCATION: (1135)..(1152)
<223> OTHER INFORMATION: hexahistidine tag
<220> FEATURE:
<221> NAME/KEY: misc_feature
<222> LOCATION: (1153)..(1155)
<223> OTHER INFORMATION: stop codon

<400> SEQUENCE: 26

```
atggtgagca agggcgagga ggataacatg gccatcatca aggagttcat gcgcttcaag      60

gtgcacatgg agggctccgt gaacggccac gagttcgaga tcgagggcga gggcgagggc     120

cgcccctacg agggcaccca gaccgccaag ctgaaggtga ccaagggtgg ccccctgccc     180

ttcgcctggg acatcctgtc ccctcagttc atgtacggct ccaaggccta cgtgaagcac     240

cccgccgaca tccccgacta cttgaagctg tccttccccg agggcttcaa gtgggagcgc     300

gtgatgaact tcgaggacgg cggcgtggtg accgtgaccc aggactcctc cctgcaggac     360

ggcgagttca tctacaaggt gaagctgcgc ggcaccaact tcccctccga cggccccgta     420

atgcagaaga agactatggg ctgggaggcc tcctccgagc ggatgtaccc cgaggacggc     480

gccctgaagg gcgagatcaa gcagaggctg aagctgaagg acggcggcca ctacgacgct     540

gaggtcaaga ccacctacaa ggccaagaag cccgtgcagc tgcccggcgc ctacaacgtc     600

aacatcaagt tggacatcac ctcccacaac gaggactaca ccatcgtgga acagtacgaa     660
```

```
cgcgccgagg gccgccactc caccggcggc atggacgagc tgtacaaggg tgacgaagtc     720

gacgaagacg aaggtgcgcg taccgtttgc tacgcggcgc acgttgaagg tatcggttgg     780

cagggtgcgg tttgcgacgg tgcggttgcg ggtaccaccg gtcagtctcg tcgtatggaa     840

gcggcggtta tcgcgacctc tggtaccggt ggtgtttgcg cgaacgcgca cctggcggac     900

atcggttggc agggttgggc gtgcgcggcg gacggtaaag cggttaccgt tggtaccacc     960

ggtcagtctc gtcgtatgga agcgctgggt ctgcaagttg gtaacggttc tgttgcggcg    1020

caggcgcacg ttgcggacta cggttggctg aacgcggaag gtggcaaccc ggtttacgtt    1080

ggcactactg gtcagtcccg tcgtatggaa gcggttcgta tctgggttct cgagcaccac    1140

caccaccacc actga                                                     1155


<210> SEQ ID NO 27
<211> LENGTH: 384
<212> TYPE: PRT
<213> ORGANISM: Artificial Sequence
<220> FEATURE:
<223> OTHER INFORMATION: mCherry1-acidic-linker-SHA
<220> FEATURE:
<221> NAME/KEY: MISC_FEATURE
<222> LOCATION: (1)..(236)
<223> OTHER INFORMATION: mCherry1
<220> FEATURE:
<221> NAME/KEY: MISC_FEATURE
<222> LOCATION: (237)..(245)
<223> OTHER INFORMATION: acidic linker
<220> FEATURE:
<221> NAME/KEY: MISC_FEATURE
<222> LOCATION: (246)..(378)
<223> OTHER INFORMATION: SHA plus Leu-Glu from cloning site
<220> FEATURE:
<221> NAME/KEY: MISC_FEATURE
<222> LOCATION: (379)..(384)
<223> OTHER INFORMATION: hexahistidine tag

<400> SEQUENCE: 27

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
```

-continued

```
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys Gly Asp Glu Val
225                 230                 235                 240

Asp Glu Asp Glu Gly Ala Arg Thr Val Cys Tyr Ala Ala His Val Glu
                245                 250                 255

Gly Ile Gly Trp Gln Gly Ala Val Cys Asp Gly Ala Val Ala Gly Thr
            260                 265                 270

Thr Gly Gln Ser Arg Arg Met Glu Ala Ala Val Ile Ala Thr Ser Gly
        275                 280                 285

Thr Gly Gly Val Cys Ala Asn Ala His Leu Ala Asp Ile Gly Trp Gln
    290                 295                 300

Gly Trp Ala Cys Ala Ala Asp Gly Lys Ala Val Thr Val Gly Thr Thr
305                 310                 315                 320

Gly Gln Ser Arg Arg Met Glu Ala Leu Gly Leu Gln Val Gly Asn Gly
                325                 330                 335

Ser Val Ala Ala Gln Ala His Val Ala Asp Tyr Gly Trp Leu Asn Ala
            340                 345                 350

Glu Gly Gly Asn Pro Val Tyr Val Gly Thr Thr Gly Gln Ser Arg Arg
        355                 360                 365

Met Glu Ala Val Arg Ile Trp Val Leu Glu His His His His His His
    370                 375                 380


<210> SEQ ID NO 28
<211> LENGTH: 145
<212> TYPE: PRT
<213> ORGANISM: Artificial Sequence
<220> FEATURE:
<223> OTHER INFORMATION: putative polysaccharide deacetylase of S.
      lavendulae

<400> SEQUENCE: 28

Val Gln Ala Ala Ala Ala Arg Gln Lys Ser Leu Ala Pro Ala Ala Arg
1               5                   10                  15

Thr Val Cys Tyr Ala Ala His Val Glu Gly Ile Gly Trp Gln Gly Ala
            20                  25                  30

Val Cys Asp Gly Ala Val Ala Gly Thr Thr Gly Gln Ser Arg Arg Met
        35                  40                  45

Glu Ala Ala Val Ile Ala Thr Ser Gly Thr Gly Gly Val Cys Ala Asn
    50                  55                  60

Ala His Leu Ala Asp Ile Gly Trp Gln Gly Trp Ala Cys Ala Ala Asp
65                  70                  75                  80

Gly Lys Ala Val Thr Val Gly Thr Thr Gly Gln Ser Arg Arg Met Glu
                85                  90                  95

Ala Leu Gly Leu Gln Val Gly Asn Gly Ser Val Ala Ala Gln Ala His
            100                 105                 110

Val Ala Asp Tyr Gly Trp Leu Asn Ala Ala Gly Gly Asn Pro Val Tyr
        115                 120                 125

Val Gly Thr Thr Gly Gln Ser Arg Arg Met Glu Ala Val Arg Ile Trp
    130                 135                 140

Val
145
```

-continued

<210> SEQ ID NO 29
<211> LENGTH: 30
<212> TYPE: PRT
<213> ORGANISM: Artificial Sequence
<220> FEATURE:
<223> OTHER INFORMATION: ArgC-digested peptide of SHA

<400> SEQUENCE: 29

```
Thr Val Cys Tyr Ala Ala His Val Glu Gly Ile Gly Trp Gln Gly Ala
1               5                   10                  15

Val Cys Asp Gly Ala Val Ala Gly Thr Thr Gly Gln Ser Arg
            20                  25                  30
```

<210> SEQ ID NO 30
<211> LENGTH: 47
<212> TYPE: PRT
<213> ORGANISM: Artificial Sequence
<220> FEATURE:
<223> OTHER INFORMATION: ArgC-digested peptide of SHA

<400> SEQUENCE: 30

```
Arg Met Glu Ala Ala Val Ile Ala Thr Ser Gly Thr Gly Gly Val Cys
1               5                   10                  15

Ala Asn Ala His Leu Ala Asp Ile Gly Trp Gln Gly Trp Ala Cys Ala
            20                  25                  30

Ala Asp Gly Lys Ala Val Thr Val Gly Thr Thr Gly Gln Ser Arg
        35                  40                  45
```

<210> SEQ ID NO 31
<211> LENGTH: 131
<212> TYPE: PRT
<213> ORGANISM: Streptomyces hemagglutinin

<400> SEQUENCE: 31

```
Ala Arg Thr Val Cys Tyr Ala Ala His Val Glu Gly Ile Gly Trp Gln
1               5                   10                  15

Gly Ala Val Cys Asp Gly Ala Val Ala Gly Thr Thr Gly Gln Ser Arg
            20                  25                  30

Arg Met Glu Ala Ala Val Ile Ala Thr Ser Gly Thr Gly Gly Val Cys
        35                  40                  45

Ala Asn Ala His Leu Ala Asp Ile Gly Trp Gln Gly Trp Ala Cys Ala
    50                  55                  60

Ala Asp Gly Lys Ala Val Thr Val Gly Thr Thr Gly Gln Ser Arg Arg
65                  70                  75                  80

Met Glu Ala Leu Gly Leu Gln Val Gly Asn Gly Ser Val Ala Ala Gln
                85                  90                  95

Ala His Val Ala Asp Tyr Gly Trp Leu Asn Ala Glu Gly Gly Asn Pro
            100                 105                 110

Val Tyr Val Gly Thr Thr Gly Gln Ser Arg Arg Met Glu Ala Val Arg
        115                 120                 125

Ile Trp Val
    130
```

<210> SEQ ID NO 32
<211> LENGTH: 131
<212> TYPE: PRT
<213> ORGANISM: Artificial Sequence
<220> FEATURE:
<223> OTHER INFORMATION: Streptomyces hemagglutinin (lost strain)

<400> SEQUENCE: 32

```
Ala Arg Thr Val Cys Tyr Ala Ala His Val Glu Gly Ile Gly Trp Gln
1               5                   10                  15

Gly Ala Val Cys Asp Gly Ala Val Ala Gly Thr Thr Gly Gln Ser Arg
            20                  25                  30

Arg Met Glu Ala Ala Val Ile Ala Thr Ser Gly Thr Gly Gly Val Cys
        35                  40                  45

Ala Asn Ala His Leu Ala Asp Ile Gly Trp Gln Gly Trp Ala Cys Ala
    50                  55                  60

Ala Asp Gly Lys Ala Val Thr Val Gly Thr Thr Gly Gln Ser Arg Arg
65                  70                  75                  80

Met Glu Ala Leu Gly Leu Gln Val Gly Asn Gly Ser Val Ala Ala Gln
                85                  90                  95

Ala His Val Ala Asp Tyr Gly Trp Leu Asn Ala Glu Gly Gly Asn Pro
            100                 105                 110

Val Tyr Val Gly Thr Thr Gly Gln Ser Arg Arg Met Glu Ala Val Arg
        115                 120                 125

Ile Trp Val
    130


<210> SEQ ID NO 33
<211> LENGTH: 199
<212> TYPE: PRT
<213> ORGANISM: S. lavendulae

<400> SEQUENCE: 33

Met Ser Arg Ala Ala Gly Val Leu Leu Gly Val Thr Leu Ala Gly Val
1               5                   10                  15

Leu Gly Ala Thr Gly Val Ala Thr Ala Gln Ala Gln Pro Ser Ala Pro
            20                  25                  30

Ala Pro Ala Pro Ser Ala Ala Ala Pro Ala Arg Ala Val Glu Ala Pro
        35                  40                  45

Ala Ser Val Ile Ala Asp Val Gln Ala Ala Ala Ala Arg Gln Lys Ser
    50                  55                  60

Leu Ala Pro Ala Ala Arg Thr Val Cys Tyr Ala Ala His Val Glu Gly
65                  70                  75                  80

Ile Gly Trp Gln Gly Ala Val Cys Asp Gly Ala Val Ala Gly Thr Thr
                85                  90                  95

Gly Gln Ser Arg Arg Met Glu Ala Ala Val Ile Ala Thr Ser Gly Thr
            100                 105                 110

Gly Gly Val Cys Ala Asn Ala His Leu Ala Asp Ile Gly Trp Gln Gly
        115                 120                 125

Trp Ala Cys Ala Ala Asp Gly Lys Ala Val Thr Val Gly Thr Thr Gly
    130                 135                 140

Gln Ser Arg Arg Met Glu Ala Leu Gly Leu Gln Val Gly Asn Gly Ser
145                 150                 155                 160

Val Ala Ala Gln Ala His Val Ala Asp Tyr Gly Trp Leu Asn Ala Glu
                165                 170                 175

Gly Gly Asn Pro Val Tyr Val Gly Thr Thr Gly Gln Ser Arg Arg Met
            180                 185                 190

Glu Ala Val Arg Ile Trp Val
        195


<210> SEQ ID NO 34
<211> LENGTH: 205
<212> TYPE: PRT
```

```
<213> ORGANISM: Artificial Sequence
<220> FEATURE:
<223> OTHER INFORMATION: S. sp. Mg1

<400> SEQUENCE: 34

Met Lys Asn Ser Met Ser Lys Ala Ala Gly Ala Val Leu Gly Leu Ala
1               5                   10                  15

Leu Ala Gly Val Leu Gly Ala Thr Gly Val Ala Gln Ala Gln Ala Leu
            20                  25                  30

Pro Ser Val Pro Ala Pro Ala Pro Ala Gly Ala Ala Val Ala Gly Pro
        35                  40                  45

Ser Ala Val Arg Ala Pro Ala Ser Val Ile Ala Gln Val Glu Ala Ala
    50                  55                  60

Thr Ala Arg Gln Arg Ala Phe Ala Pro Asn Ala Arg Thr Val Cys Tyr
65                  70                  75                  80

Ala Ala His Val Glu Gly Ile Gly Trp Gln Gly Ala Val Cys Asp Gly
                85                  90                  95

Ala Val Ala Gly Thr Thr Gly Gln Ser Arg Arg Met Glu Ala Ala Val
            100                 105                 110

Ile Ala Thr Ser Gly Thr Gly Gly Val Cys Ala Asn Ala His Leu Ala
        115                 120                 125

Asp Ile Gly Trp Gln Gly Trp Ala Cys Ala Ala Asp Gly Lys Ala Val
    130                 135                 140

Thr Val Gly Thr Thr Gly Gln Ser Arg Arg Met Glu Ala Leu Gly Leu
145                 150                 155                 160

Gln Val Gly Asn Gly Ser Val Ala Ala Gln Ala His Val Ala Asp Tyr
                165                 170                 175

Gly Trp Leu Asn Ala Ala Gly Gly Asn Pro Val Tyr Val Gly Thr Thr
            180                 185                 190

Gly Gln Ser Arg Arg Met Glu Ala Val Arg Ile Trp Val
        195                 200                 205


<210> SEQ ID NO 35
<211> LENGTH: 203
<212> TYPE: PRT
<213> ORGANISM: Artificial Sequence
<220> FEATURE:
<223> OTHER INFORMATION: S. sp. Wm4235

<400> SEQUENCE: 35

Met Lys Ser Ser Met Ser Arg Val Ala Gly Ala Val Leu Gly Met Ala
1               5                   10                  15

Leu Ala Gly Val Leu Gly Ala Thr Gly Val Ala Gln Ala Gln Gly Arg
            20                  25                  30

Pro Ser Ala Pro Ala Pro Ala Ser Gly Arg Ala Val Ala Ser Gly Ala
        35                  40                  45

Val Gln Ala Pro Ala Ala Val Ile Ala Glu Val Glu Ala Ala Thr Ala
    50                  55                  60

Arg Gln Arg Ser Leu Ala Pro Asn Ala Arg Thr Val Cys Tyr Ala Ala
65                  70                  75                  80

His Val Gln Asp Val Gly Trp Gln Ala Ala Val Cys Asp Gly Gln Val
                85                  90                  95

Ala Gly Thr Thr Gly Gln Gly Arg Arg Met Glu Ala Val Val Ile Ala
            100                 105                 110

Thr Arg Gly Val Gly Gly Val Cys Ala Asn Ala His Leu Ala Asp Val
        115                 120                 125
```

-continued

```
Gly Trp Gln Gly Trp Ala Cys Ala Gly Glu Gly Ala Ala Val Thr Val
    130                 135                 140

Gly Thr Thr Gly Gln Ala Arg Arg Met Glu Ala Leu Gly Val Gln Val
145                 150                 155                 160

Gly Ser Gly Gly Val Gly Ala Gln Ala His Val Ala Asn His Gly Trp
                165                 170                 175

Leu Asn Thr Val Ala Gly Asn Pro Val Tyr Ala Gly Thr Thr Gly Gln
            180                 185                 190

Ala Leu Arg Met Glu Ala Val Arg Ile Trp Val
        195                 200


<210> SEQ ID NO 36
<211> LENGTH: 204
<212> TYPE: PRT
<213> ORGANISM: S. xanthophaeus

<400> SEQUENCE: 36

Met Lys Ile Ser Arg Ser Ser Thr Ala Ala Ala Val Leu Gly Thr Ala
1               5                   10                  15

Leu Ala Cys Val Leu Gly Ala Ala Gly Ala Ala Gly Ala Gln Gln Gln
            20                  25                  30

Pro Ala Pro Ala Pro Ala Pro Ala Asn Ala Ala Ser Val Ala Ala Gly
        35                  40                  45

Ser Ala Val Gln Ala Pro Ala Ala Val Val Gly Glu Leu Lys Ala Ala
    50                  55                  60

Thr Ala Arg Ala Ser Leu Ala Pro Gly Ala Arg Ala Val Cys Tyr Ala
65                  70                  75                  80

Ala His Val Gln Asp Val Gly Trp Gln Pro Thr Val Cys Asn Gly Glu
                85                  90                  95

Val Ala Gly Thr Thr Gly Gln Gly Arg Arg Ile Glu Ala Val Leu Ile
            100                 105                 110

Ser Thr Gly Gly Val Gly Gly Ile Cys Ala Asn Ala His Leu Ala Asp
        115                 120                 125

Val Gly Trp Gln Gly Trp Ala Cys Ala Gly Asp Gly Thr Val Val Gly
    130                 135                 140

Val Gly Thr Thr Gly Gln Ser Arg Arg Met Glu Ala Leu Gly Leu Gln
145                 150                 155                 160

Ala Gly Ser Gly Ser Val Ala Ala Gln Ala His Val Gln Asp His Ala
                165                 170                 175

Trp Leu Asn Ala Val Gly Gly Asn Pro Val Tyr Val Gly Thr Thr Gly
            180                 185                 190

Gln Ser Arg Arg Met Glu Ala Leu Arg Val Trp Val
        195                 200


<210> SEQ ID NO 37
<211> LENGTH: 146
<212> TYPE: PRT
<213> ORGANISM: Artificial Sequence
<220> FEATURE:
<223> OTHER INFORMATION: S. sp. Wm6378

<400> SEQUENCE: 37

Met Lys Ala Ala Thr Ser Arg Ala Arg Ala Ser Leu Ser Pro Asn Ala
1               5                   10                  15

Arg Val Ile Cys Tyr Ala Ala His Val Gln Asp Ile Gly Trp Gln Ser
            20                  25                  30

Ala Val Cys Asp Gly Ser Val Ala Gly Thr Thr Gly Gln Ser Arg Arg
```

```
        35                  40                  45

Met Glu Ala Leu Ala Ile Ser Thr Ser Gly Val Gly Gly Val Cys Ala
    50                  55                  60

Asp Ala His Leu Ala Asp Ile Gly Trp Gln Gly Trp Arg Cys Gly Gly
65                  70                  75                  80

Asp Gly Thr Val Val Thr Val Gly Thr Thr Gly Gln Ser Arg Arg Met
                85                  90                  95

Glu Ala Leu Gly Val Gln Val Gly Thr Gly Ser Val Gly Ala Gln Ala
            100                 105                 110

His Val Glu Gly Tyr Gly Trp Leu Ser Ser Val Thr Gly Asn Pro Val
        115                 120                 125

Tyr Val Gly Thr Thr Gly Gln Ser Arg Arg Met Glu Ala Val Arg Ile
    130                 135                 140

Trp Val
145


<210> SEQ ID NO 38
<211> LENGTH: 205
<212> TYPE: PRT
<213> ORGANISM: Streptacidiphilus melanog.

<400> SEQUENCE: 38

Met Phe Thr Leu Thr Arg Arg Gly Ala Val Leu Ala Ala Ala Gly Leu
1               5                   10                  15

Leu Ala Ala Gly Leu Ser Ala Ala Ala Pro Gly Gly Thr Ala Phe Ala
            20                  25                  30

Ala Gly His Thr Thr Ala Thr Arg Thr Thr Thr Ala Ala Thr Gly Ala
        35                  40                  45

Asp Ala Gln Arg Gln Ala Ala Leu Val Ala Ala Val Lys Arg Gln Ala
    50                  55                  60

Ala Leu His Pro Asn Ala Ser Gly Arg His Ile Cys Tyr Ala Ala His
65                  70                  75                  80

Val Gln Asn Ile Gly Trp Gln Thr Pro Val Cys Asp Gly Ala Met Ala
                85                  90                  95

Gly Thr Thr Gly Gln Ser Leu Arg Met Glu Ala Leu Asp Ile Ala Val
            100                 105                 110

Ser Gly Val Gly Gly Val Cys Ala Asp Ala His Val Gln Asn Ile Gly
        115                 120                 125

Trp Gln Gly Trp Ala Cys Ala Gly Asp Asn Val Asp Val Tyr Val Gly
    130                 135                 140

Thr Thr Gly Gln Ser Leu Arg Met Glu Ala Leu Gln Ile Asn Val Ala
145                 150                 155                 160

Ser Gly Thr Val Cys Ala Asp Ala His Val Gln Asn Ile Gly Trp Gln
                165                 170                 175

Gly Trp Ala Cys Ala Ala Ala Gly Ser Thr Ala Val Val Gly Thr Thr
            180                 185                 190

Gly Gln Ser Leu Arg Met Glu Ala Ile Glu Leu Thr Val
        195                 200                 205


<210> SEQ ID NO 39
<211> LENGTH: 265
<212> TYPE: PRT
<213> ORGANISM: S. clavuligerus

<400> SEQUENCE: 39

Met Tyr Gly Trp Pro Ala Arg Arg Trp Cys Gly Gly Arg Pro Pro Gly
```

-continued

```
1               5                   10                  15

Pro Val Pro Ser Gly Thr Gly Pro Cys Asp Pro Thr Gly Ala Arg His
            20                  25                  30

Ser Ala Arg Phe Ser Gly Gln Arg Pro Thr Ala Val Ser Pro Ser Pro
        35                  40                  45

Ala Pro Leu Ala Thr Tyr Ser Ala Ala Val Arg Lys Thr Leu Arg Ser
    50                  55                  60

Thr Arg Gly Arg Ser Gly Met Asn Gln Pro Gly Ser Arg Gly Thr Val
65                  70                  75                  80

Arg Ala Leu Leu Ala Leu Gly Leu Val Gly Ala Phe Gly Phe Ala Gly
                85                  90                  95

Ala Gly Thr Ala Ala Gln Ala Gln Glu Arg Val Ser Gly Ala Gly Gly
            100                 105                 110

Tyr Ala Ala Gly Thr Thr Ala Ala Glu Ala Leu Arg Ala Glu Leu Gly
        115                 120                 125

Arg Arg Gly Thr Ala Ala Ala Arg Ser Val Cys Tyr Arg Ala His Val
    130                 135                 140

Thr Gly Ile Gly Trp Leu Ala Pro Val Cys Asn Gly Gly Leu Ala Gly
145                 150                 155                 160

Ser Val Gly Gly Asn Arg Ala Val Glu Ala Val Glu Ile Ala Thr Ser
                165                 170                 175

Glu Thr Gly Gly Ile Cys Ala Gly Ala His Leu Ala Asp Leu Gly Trp
            180                 185                 190

Glu Arg Thr Arg Cys Ala Pro Asn Gly Ala Ser Val Thr Val Gly Thr
        195                 200                 205

Thr Gly Glu Ser Arg Ala Met Glu Ala Leu Thr Leu Glu Thr Gly Leu
    210                 215                 220

Gly Ala Met Ala Ala Gln Gly His Val Gln Asp Leu Gly Trp Met Glu
225                 230                 235                 240

Pro Gln Ala Gly Leu Ser Val Thr Val Gly Thr Thr Gly Arg His Lys
                245                 250                 255

Arg Leu Glu Ala Ile Arg Val Trp Val
            260                 265


<210> SEQ ID NO 40
<211> LENGTH: 208
<212> TYPE: PRT
<213> ORGANISM: S. scabiei

<400> SEQUENCE: 40

Met Tyr Lys Arg Ala Ser Leu Val Gly Ala Ala Ala Leu Thr Ala Val
1               5                   10                  15

Ala Phe Thr Ala Pro Val Ala Gln Ala Ala Glu Pro Ala Gln Thr Gly
            20                  25                  30

Thr Thr Ala Ile Thr Arg Ala Met Pro Asp Gly Glu Leu Gln Ala Asp
        35                  40                  45

Gly Ser Thr Arg Tyr Gly Gln Gly Val Ser Leu Ala Glu Ala Ile Lys
    50                  55                  60

Ala Glu Arg Ala Arg Leu Gly Lys Ser Thr Ala Ala Ala Arg Ser Val
65                  70                  75                  80

Cys Tyr Arg Ala His Val Ala Gly Leu Gly Trp Gln Ala Val Val Cys
                85                  90                  95

Asn Gly Gly Thr Ala Gly Thr Glu Gly Gln Ser Arg Ala Met Glu Ala
            100                 105                 110
```

-continued

Leu Glu Val Ala Val Gly Gly Ala Gly Glu Phe Cys Val Asn Ala His
115 120 125

Leu Arg Asn Ile Gly Trp Gln Ala Glu Ala Tyr Cys Ala Asn Asp Gly
130 135 140

Gly Thr Val Arg Val Gly Thr Val Gly Gln Ala Arg Pro Met Glu Ala
145 150 155 160

Val Met Ile Gly Val Ser Ser Gly Ala Val Lys Gly Arg Ala His Val
165 170 175

Gln Asn Ile Gly Trp Leu Ala Pro Gln Asp Asp Ala Val Ile Thr Leu
180 185 190

Gly Thr Thr Ala Gln Thr Arg Asn Leu Glu Ala Val Arg Ile Trp Leu
195 200 205

<210> SEQ ID NO 41
<211> LENGTH: 198
<212> TYPE: PRT
<213> ORGANISM: Artificial Sequence
<220> FEATURE:
<223> OTHER INFORMATION: Lentzea sp. DHS C013

<400> SEQUENCE: 41

Met His Arg Arg Tyr Arg Phe Ala Ala Leu Leu Ala Thr Ala Phe Thr
1 5 10 15

Ala Leu Gly Leu Thr Ala Ala Pro Ala Asn Ala Asp Thr Ala Pro Asn
20 25 30

Ala Thr Thr Gly Ala Pro Gly Ser Ala Lys Ser Asn Ser Ser Ile Gln
35 40 45

Ala Pro Ala Leu Pro Asp Gln Leu Arg Ala Gln Ala Ala Arg Thr Val
50 55 60

Cys Leu Asn Ala His Leu Glu Asn Val Gly Trp Gln Gly Trp Val Cys
65 70 75 80

Ala Ser Asp Gly Ala Gly Ala Leu Val Gly Thr Gly Gln Asn Arg Gln
85 90 95

Met Glu Ala Leu Ala Val Ser Ser Ala Gly Thr Gly Gly Ile Cys Ala
100 105 110

Gln Ala His Val Ala Asp Leu Gly Trp Leu Ser Gln Val Cys Val Ala
115 120 125

Asp Gly Asp Val Gly Val Val Gly Thr Thr Gly Gln Gly Arg Gln Val
130 135 140

Glu Ala Leu Gly Leu Gly Ala Pro Ser Ala Thr Thr Cys Ala Asn Ala
145 150 155 160

His Leu Ser Gly Ile Gly Trp Gln Gly Ala Ser Cys Ala Gly Pro Gly
165 170 175

Val Val Ala Phe Val Gly Thr Thr Gly Gln Asn Arg Gln Met Glu Ala
180 185 190

Leu Ile Ala Gly Val Ser
195

<210> SEQ ID NO 42
<211> LENGTH: 172
<212> TYPE: PRT
<213> ORGANISM: Actinobacteria bacterium

<400> SEQUENCE: 42

Met Arg Lys Ala Leu Gly Thr Val Leu Ala Ser Val Ala Leu Thr Val
1 5 10 15

Gly Ser Thr Val Ala Leu Ala Ala Pro Ala Ser Ala Ala Asp Asn Ser

```
            20                  25                  30

Ala Ala Gly Ala Ala Ala Ala Ala Ser Gly Thr Ala Ile Cys Tyr Gln
        35                  40                  45

Ala His Val Arg Asn Ile Gly Trp Gln Gly Thr Val Cys Asn Gly Thr
    50                  55                  60

Met Ala Gly Thr Thr Gly Lys Asn Leu Gly Ile Glu Ala Leu Thr Val
65                  70                  75                  80

Ala Thr Ala Gly Thr Gly Gly Leu Cys Leu Gln Ala His Val Gln Asn
                85                  90                  95

Ile Gly Trp Gln Asn Lys Val Cys Ala Ala Asp Gly Gln Asn Leu Thr
            100                 105                 110

Val Gly Thr Thr Gly Arg Gly Leu Asn Ile Glu Ala Leu Ile Ile Ser
        115                 120                 125

Thr Gly Thr Gly Val Ser Ala Asn Gly His Phe Ser Asn Tyr Gly Trp
    130                 135                 140

Thr Gly Trp Ser Gly Tyr Ala Tyr Glu Val Ala Ile Gly Ser Thr Gly
145                 150                 155                 160

Gln Asn Arg Ala Met Glu Ala Ile Ala Leu Ala Val
                165                 170


<210> SEQ ID NO 43
<211> LENGTH: 199
<212> TYPE: PRT
<213> ORGANISM: Artificial Sequence
<220> FEATURE:
<223> OTHER INFORMATION: Nocardia. sp. NRRL S-836

<400> SEQUENCE: 43

Met His Arg Arg Phe Arg Phe Ala Ala Leu Leu Thr Thr Ala Leu Thr
1               5                   10                  15

Ala Leu Ala Leu Thr Ala Ala Pro Ala Thr Ala Ala Thr Gly Pro Asn
            20                  25                  30

Thr Thr Thr Gly Val Pro Gly Pro Ser Lys Ser Asn Ser Ala Val Gln
        35                  40                  45

Ala Pro Ala Leu Pro Asp Pro Leu Arg Ala Gln Ala Ala Arg Thr Val
    50                  55                  60

Cys Leu Asn Ala His Leu Ala Gly Thr Gly Trp Gln Gly Trp Val Cys
65                  70                  75                  80

Ala Ser Asp Gly Val Gly Ala Leu Val Gly Thr Thr Gly Gln Ser Arg
                85                  90                  95

Gln Met Glu Ala Leu Ala Val Ser Ser Ala Gly Thr Gly Gly Phe Cys
            100                 105                 110

Thr Gln Ala His Val Gly Gly Leu Gly Trp Leu Ser Gln Val Cys Val
        115                 120                 125

Ala Asp Gly Asn Val Gly Val Val Gly Thr Thr Gly Gln Gly Arg Ala
    130                 135                 140

Ile Glu Ala Leu Gly Leu Gly Ala Pro Ala Ala Thr Thr Cys Ala Asn
145                 150                 155                 160

Ala His Leu Ser Gly Thr Gly Trp Gln Gly Ala Thr Cys Ala Gly Pro
                165                 170                 175

Thr Val Val Ala Leu Val Gly Thr Thr Gly Gln Ser Arg Gln Met Glu
            180                 185                 190

Ala Leu Val Ala Ala Val Gly
        195
```

-continued

```
<210> SEQ ID NO 44
<211> LENGTH: 29
<212> TYPE: PRT
<213> ORGANISM: Streptomyces hemagglutinin

<400> SEQUENCE: 44

Ala His Val Glu Gly Ile Gly Trp Gln Gly Ala Val Cys Asp Gly Ala
1               5                   10                  15

Val Ala Gly Thr Thr Gly Gln Ser Arg Arg Met Glu Ala
            20                  25


<210> SEQ ID NO 45
<211> LENGTH: 33
<212> TYPE: PRT
<213> ORGANISM: Streptomyces hemagglutinin

<400> SEQUENCE: 45

Ala His Leu Ala Asp Ile Gly Trp Gln Gly Trp Ala Cys Ala Ala Asp
1               5                   10                  15

Gly Lys Ala Val Thr Val Gly Thr Thr Gly Gln Ser Arg Arg Met Glu
            20                  25                  30

Ala


<210> SEQ ID NO 46
<211> LENGTH: 30
<212> TYPE: PRT
<213> ORGANISM: Streptomyces hemagglutinin

<400> SEQUENCE: 46

Ala His Val Ala Asp Tyr Gly Trp Leu Asn Ala Glu Gly Gly Asn Pro
1               5                   10                  15

Val Tyr Val Gly Thr Thr Gly Gln Ser Arg Arg Met Glu Ala
            20                  25                  30
```

RECOMBINANT LECTIN AND USES THEREOF

CROSS-REFERENCE TO RELATED APPLICATIONS

The present invention is a divisional application of U.S. application Ser. No. 16/165,725, filed Oct. 19, 2018, which claims priority to U.S. Provisional Application Nos. 62/574,626 and 62/574,636, both filed on Oct. 19, 2017, the contents of which are incorporated herein by reference in their entireties, including the drawings.

STATEMENT OF GOVERNMENT INTEREST

This invention was made with government support under Grant Number CA033572, awarded by the National Institutes of Health. The Government has certain rights in the invention.

SEQUENCE LISTING

This application contains a Sequence Listing, which was submitted in ASCII format via EFS-Web, and is hereby incorporated by reference in its entirety. The ASCII copy, created on Aug. 4, 2021, is named SequenceListing.txt and is 38 KB in size.

BACKGROUND

In 1972, culture supernatants of 333 Actinomycetales bacterial strains isolated from the greater Tokyo area were screened for hem agglutination activity to identify microbial lectins (1,2). The culture supernatant of *Streptomyces* sp. 27S5 exhibited blood type B-specific activity. This was very unique at the time, because previously-known plant lectins were either A- or O-blood type-specific. Sixty mg of the identified lectin, named *Streptomyces* hemagglutinin (SHA), was purified to homogeneity from a 15-L culture broth of S. sp. 27S5 using gum arabic affinity chromatography, achieving a 13,300-fold enrichment with 64% recovery of the total activity (3). More than 200 mg of SHA was ultimately purified and subjected to various analyses. SHA was characterized as a small protein (~11 kDa) with unique characteristics, such as rare blood type B specificity, an atypical tryptophan-rich nature, and two carbohydrate-binding sites (3,4). Accordingly, further study of SHA is needed.

SUMMARY

This disclosure relates to characterization, production of a recombinant SHA and homologues thereof and a fusion protein of a fluorescent protein and SHA that specifically bind to L-rhamnose or D-galactose, and novel uses of SHA and the fusion protein in detecting microorganisms that express carbohydrates containing L-rhamnose or D-galactose on the surface, or detecting tumor-expressed carbohydrates capable of specifically binding to SHA. Certain cancer/tumor cells expressing carbohydrates containing D-galactose on the surface can be detected by the methods disclosed herein. In some embodiments, the fusion protein is a fusion protein of a green fluorescent protein and SHA (GFP-SHA). In some embodiments, the fusion protein is a fusion protein of a red fluorescent protein and SHA (mCherry1-SHA). In some embodiments, the fusion protein is a non-aggregating protein. In some embodiments, the fusion protein is a soluble protein that is stable at about 4° C. for an extended period of time. In some embodiments, the fluorescent protein is linked to the N-terminus of SHA. In some embodiments, the fluorescent protein is linked to the C-terminus of SHA. In some embodiments, the fluorescent protein and SHA are linked via an acidic linker.

In one aspect, the disclosure provided herein relates to a recombinant *Streptomyces* S27S5 hemagglutinin (SHA), homologues thereof, and fusions proteins of a fluorescent protein (such as GFP or mCherry1) and SHA or homologues thereof (GFP-SHA fusion proteins or mCherry1-SHA fusion proteins). SHA, homologues thereof, SHA or homologues labeled with a marker such as a fluorescein or a derivative thereof, and GFP-SHA or mCherry1-SHA fusion proteins specifically bind to carbohydrates, including oligomeric sugars that terminate in L-rhamnose or D-galactose.

In another aspect, the disclosure provided herein relates to a method for detecting a microbial infection in a subject, wherein the microbial cell expresses a carbohydrate containing L-rhamnose or D-galactose on the surface. The method includes contacting a fluorescein or a derivative thereof labeled SHA or a fusion protein of a fluorescent protein and SHA disclosed herein with a sample from the subject, and detecting the fluorescence level in the sample, wherein the detection of fluorescence in the sample indicates the presence of the microbial infection. In some embodiments, the fusion protein is a fusion protein of a green fluorescent protein and SHA (GFP-SHA). In some embodiments, the fusion protein is a fusion protein of a red fluorescent protein and SHA (mCherry1-SHA). In some embodiments, the SHA is labeled with a fluorescein derivative such as fluorescein isothiocyanate (FITC). In some embodiments, the sample includes a biopsy sample, a tissue sample, a bronchoalveolar lavage sample, a blood sample, and a urine sample. In some embodiments, the microbial infection is caused by a bacterium or a fungus that expresses dTDP-4-dehydrorhamnose reductase gene (rmlD). In some embodiments, the microbial infection includes mycoses caused by *Candida albicans, Aspergillus fumigatus*, or *Fusarium solani*. In some embodiments, the microbial infection is an infection by *Streptococcus, Enterococcus* or *Lactococcus*. In some embodiments, the microbial infection is invasive pulmonary aspergillosis, and the GFP-SHA fusion protein disclosed herein detects the presence of fungal galactomannan, indicating invasive pulmonary aspergillosis.

In another aspect, the disclosure provided herein relates to a method for detecting a cancer or tumor in a subject, wherein the cancer or tumor cell expresses a carbohydrate capable of specifically binding to SHA, a homologue thereof, a fragment of the SHA or a homologue thereof, a fluorescein or a derivative thereof labeled SHA, a homologue or fragment of the SHA, or a fusion protein of a fluorescent protein and SHA disclosed herein. In some embodiments, the cancer or tumor cell express a surface antigen containing D-galactose. In some embodiments, the method includes contacting a fluorescein or a derivative thereof labeled SHA, or a fusion protein of a fluorescent protein and SHA disclosed herein with a sample from the subject, and detecting the fluorescence level in the sample, wherein the detection of fluorescence in the sample indicates the presence of the cancer or tumor cell. In some embodiments, the sample includes a biopsy sample, a tissue sample, a bronchoalveolar lavage sample, a blood sample, and a urine sample. In some embodiments, the cancer includes colon cancer, pancreatic ductal carcinoma and pancreatic cancer. In some embodiments, the fusion protein is a fusion protein of a green fluorescent protein and SHA (GFP-SHA). In some embodiments, the fusion protein is a fusion protein of a red fluorescent protein and SHA (mCherry1-SHA). In some embodiments, the SHA is labeled with a fluorescein derivative such as fluorescein isothiocyanate (FITC).

In another aspect, the disclosure provided herein relates to a positron emission tomography (PET) probe comprising an SHA protein, a homologue thereof, a functional fragment of SHA or a homologue thereof, a fluorescein or a derivative thereof labeled SHA or a homologue or fragment of the SHA, or a fusion protein of a fluorescent protein and SHA disclosed herein labeled with a positron-emitting isotope. In some embodiments, the fusion protein is a fusion protein of a green fluorescent protein and SHA (GFP-SHA). In some embodiments, the fusion protein is a fusion protein of a red fluorescent protein and SHA (mCherry1-SHA). In some embodiments, the SHA is labeled with a fluorescein derivative such as fluorescein isothiocyanate (FITC).

In a related aspect, the disclosure relates to a method of imaging an organ or tissue having a microbial infection or detecting a location having a microbial infection caused by a microorganism expressing a carbohydrate containing L-rhamnose or D-galactose on the surface. The method entails administering to a subject suffering from or suspected of suffering from a microbial infection the PET probe described above, and imaging the organ or the tissue having the microbial infection by a PET scanning of the subject. Alternatively, the method entails administering to a subject suffering from or suspected of suffering from a microbial infection the PET probe described above, and detecting the location of the PET probe, thereby determining the location of the microbial infection. In some embodiments, the PET probe is locally administered to the subject. In some embodiments, the PET probe is systemically administered to the subject, e.g., by intravenous injection.

In yet another related aspect, the disclosure relates to a method of imaging a tumor or detecting a location having a cancer or tumor, where the cancer or tumor cell expresses an antigen comprising a carbohydrate capable of specifically binding to SHA, a homologue thereof, a fragment of the SHA and a homologue thereof, or a fluorescein labeled SHA or a homologue or fragment of the SHA. The method entails administering to a subject suffering from or suspected of suffering from a cancer or tumor the PET probe described above, and imaging the organ or the tissue having the cancer or tumor by a PET scanning of the subject. Alternatively, the method entails administering to a subject suffering from or suspected of suffering from a cancer or tumor the PET probe described above, and detecting the location of the PET probe, thereby determining the location of the cancer or tumor cells. In some embodiments, the PET probe is locally administered to the subject. In some embodiments, the PET probe is systemically administered to the subject, e.g., by intravenous injection.

BRIEF DESCRIPTION OF THE DRAWINGS

This application contains at least one drawing executed in color. Copies of this application with color drawing(s) will be provided by the Office upon request and payment of the necessary fees.

FIGS. 5A and 5B show that a single amino acid difference between recombinant SHA and the putative SHA domain of PDSL was identified by MALDI-MS of peptides from SHA and Trx-SHA, obtained after digestion with trypsin and LysC (5A) or ArgC (5B). FIG. 5C shows Orbitrap LC-MS of two ArgC-digested peptides of SHA before (non-reduced) and after (reduced) reduction with TCEP. FIG. 5 shows the sequence and primary structure of SHA derived from the results in FIGS. 5A-5C. Fragments identified by MS analyses (5A, 5B) are indicated by blue lines; S—S bonds identified by Orbitrap LC-MS (comparisons within 5C) are indicated by red linking lines; the A to E mutation at SHA position 108 (indicated by green labeled peak in 5A, and by blue linking lines in 5B) is highlighted in red.

FIG. 6A shows representative heat maps of glycan-specific fluorescent signals (raw data in FIG. 7) in the absence (left panel) or in presence of 0.2 M L-rhamnose (right panel) using two different concentrations (1×, 0.1×) of SHA (top) or rSHA (bottom). FIG. 6B shows quantification of the normalized fluorescent glycan binding signals for archived and recombinant SHA, as in FIG. 6A (n=4). POS1-3 are positive controls containing standardized amounts of biotinylated IgGs; NEG are negative controls; numbers mark array positions of glycans with positive binding signals, as listed in FIG. 6B. Linker molecules are SP: $OCH_2CH_2CH_2NH_2$ and SP1: $NH(CH_3)OCH_2CH_2NH_2$. All other glycans that did not bind SHA/rSHA are listed in Table 4. FIG. 6C shows SDS-PAGE analysis of purified rSHA and archived SHA on a 4-12% gradient gel and visualized with Coomassie Blue staining.

FIG. 8A shows cross-species amino acid sequence comparison of SHA and the 11 closest SHA homologues. The boxes indicate SHA domains. Solid lines indicate experimentally defined disulfide bonds in SHA. FIG. 8B shows phylogenetic tree of SHA homologues (left). For percent sequence identity for proteins (center), number of identical residues/number of query residues matched are indicated in parentheses. Matching query length>131 indicates additional residues within the SHA homologues. For DNA (right), *S. lavendulae* DNA (438 bases) was used as the reference query for SHA homologues. Data are shown as percent identity/percent query covered of the corresponding nucleotide sequence. FIG. 8C shows comparison of the three SHA domains in the SHA protein.

DETAILED DESCRIPTION

Figure 1:
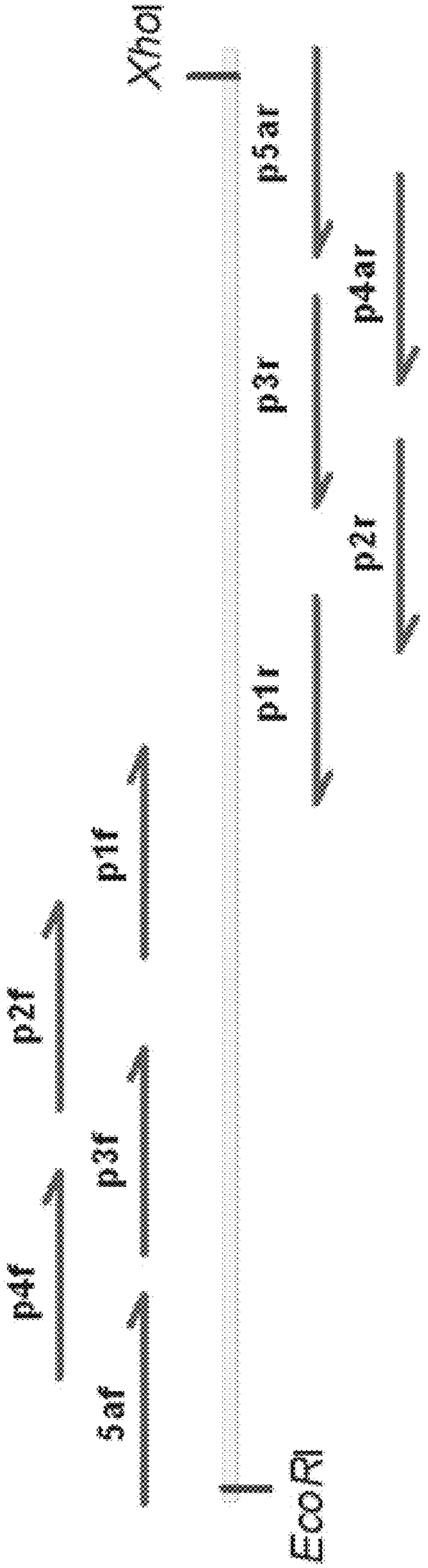
FIG. 1 illustrates the primer design for construction of rSHA.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

In one aspect, disclosed herein is a fusion protein, the amino acid sequence of which fusion protein comprising the amino acid sequence of a fluorescent protein and the amino acid sequence of SHA or an SHA homologue, and which fusion protein specifically binds to L-rhamnose or D-galactose. SHA or the SHA homologue specifically binds to L-rhamnose or D-galactose, and fusion to a fluorescent protein allows fluorescent detection of the SHA protein while retaining the specific binding to L-rhamnose or D-galactose. In some embodiments, the fluorescent protein includes GFP and mCherry1.

In some embodiments, SHA or the homologue thereof is a recombinant protein. In some embodiments, the amino acid sequence of SHA comprises three domains represented by SEQ ID NO: 17, SEQ ID NO: 19, and SEQ ID NO: 21, respectively. In some embodiments, each of the three domains comprises SEQ ID NO: 24 at the C-terminus. In some embodiments, the recombinant SHA (rSHA) has the following amino acid sequence:

```
                                          (SEQ ID NO: 25)
ARTVCYAAHVEGIGWQGAVCDGAVAGTTGQSRRMEAAVIATSGTGGVCAN

AHLADIGWQGWACAADGKAVTVGTTGQSRRMEALGLQVGNGSVAAQAHVA

DYGWLNAEGGNPVYVGTTGQSRRMEAVRIVVV.
```

In some embodiments, the amino acid sequence of the SHA homologue is at least 70%, at least 75%, at least 80%, at least 85%, at least 90%, at least 95%, at least 98%, or at least 99% identical to SEQ ID NO: 25. In some embodiments, the amino acid sequence of the SHA homologue is codon optimized.

In some embodiments, the fusion proteins encompassed in this disclosure include fusion proteins comprising GFP and a functional fragment of SEQ ID NO: 25 or a homologue thereof, as long as the functional fragment and the fusion protein of the GFP-SHA functional fragment are able to specifically bind to L-rhamnose and/or D-galactose. For example, a functional fragment of SEQ ID NO: 25 is a peptide homologous to a consecutive sequence of SEQ ID NO: 25 having substantially the same or even improved binding affinity to L-rhamnose and/or D-galactose comparing to the full length SHA protein represented by SEQ ID NO: 25. In some embodiments, the functional fragment is at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 110 amino acids, or at least 120 amino acids in length.

In some embodiments, the fusion proteins encompassed in this disclosure include fusion proteins comprising mCherry1 and a functional fragment of SEQ ID NO: 25 or a homologue thereof, as long as the functional fragment and the fusion protein of the mCherry1-SHA functional fragment are able to specifically bind to L-rhamnose and/or D-galactose. For example, a functional fragment of SEQ ID NO: 25 is a peptide homologous to a consecutive sequence of SEQ ID NO: 25 having substantially the same or even improved binding affinity to L-rhamnose and/or D-galactose comparing to the full length SHA protein represented by SEQ ID NO: 25. In some embodiments, the functional fragment is at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 110 amino acids, or at least 120 amino acids in length.

In some embodiments, mCherry1 and SHA are fused via an acidic linker with the sequences shown below. In some embodiments, the acidic linker increases solubility of the fusion proteins.

mCherry1-acidic-linker-SHA DNA sequence (SEQ ID NO: 26) (bases 1-708: mCherry1 (shown in capital letters); bases 709-735: acidic linker (shown in small letters, underlined); bases 736-1128: SHA (shown in capital letters, italic); bases 1129-1134: XhoI cloning site (shown in small letters, italic, underlined); bases 1135-1152: hexahistidine tag (shown in small letters); and bases 1153-1155: stop codon (shown in capital letters, bold):

[1]ATGGTGAGCAAGGGCGAGGAGGATAACATGGCCATCATCAAGGAGTTCA
TGCGCTTCAAGGIGCACATGGAGGGCTCCGTGAACGGCCACGAGTTCGAG
ATCGAGGGCGAGGGCGAGGGCCGCCCCTACGAGGGCACCCAGACCGCCAA
GCTGAAGGTGACCAAGGGTGGCCCCCTGCCCTTCGCCTGGGACATCCTGT
CCCCTCAGTTCATGTACGGCTCCAAGGCCTACGTGAAGCACCCCGCCGAC
ATCCCCGACTACTTGAAGCTGTCCTTCCCCGAGGGCTTCAAGTGGGAGCG
CGTGATGAACTTCGAGGACGGCGGCGTGGTGACCGTGACCCAGGACTCCT
CCCTGCAGGACGGCGAGTTCATCTACAAGGTGAAGCTGCGCGGCACCAAC
TTCCCCTCCGACGGCCCCGTAATGCAGAAGAAGACTATGGGCTGGGAGGC
CTCCTCCGAGCGGATGTACCCCGAGGACGGCGCCCTGAAGGGCGAGATCA
AGCAGAGGCTGAAGCTGAAGGACGGCGGCCACTACGACGCTGAGGTCAAG
ACCACCTACAAGGCCAAGAAGCCCGTGCAGCTGCCCGGCGCCTACAACGT
CAACATCAAGTTGGACATCACCTCCCACAACGAGGACTACACCATCGTGG
AACAGTACGAACGCGCCGAGGGCCGCCACTCCACCGGCGGCATGGACGAG
CTGTACAAG[709]ggtgacgaagtcgacgaagacgaaggt[736]*GCGCGTAC*
*CGTTTGCTACGCGGCGCACGTTGAAGGTATCGGTTGGCAGGGTGCGGTTT*
*GCGACGGTGCGGTTGCGGGTACCACCGGTCAGTCTCGTCGTATGGAAGCG*
*GCGGTTATCGCGACCTCTGGTACCGGTGGTGTTTGCGCGAACGCGCACCT*
*GGCGGACATCGGTTGGCAGGGTTGGGCGTGCGCGGCGGACGGTAAAGCGG*
*TTACCGTTGGTACCACCGGTCAGTCTCGTCGTATGGAAGCGCTGGGTCTG*
*CAAGTTGGTAACGGTTCTGTTGCGGCGCAGGCGCACGTTGCGGACTACGG*
*TTGGCTGAACGCGGAAGGTGGCAACCCGGTTTACGTTGGCACTACTGGTC*
*AGTCCCGTCGTATGGAAGCGGTTCGTATCTGGGTT*[1129]*ctcgag*[1135]c
accaccaccaccaccac[1153]TGA mCherry1-acidic-linker-SHA protein sequence (SEQ ID NO: 27) (AA 1-236: mCherry1; AA 237-245: acidic linker (italic, underlined); AA 246-378: SHA plus Leu-Glu from cloning site; and AA 379-384: hexahistidine tag):

[1]Met-Val-Ser-Lys-Gly-Glu-Glu-Asp-Asn-Met-Ala-
Ile-Ile-Lys-Glu-Phe-Met-Arg-Phe-Lys-Val-His-Met-
Glu-Gly-Ser-Val-Asn-Gly-His-Glu-Phe-Glu-Ile-Glu-
Gly-Glu-Gly-Glu-Gly-Arg-Pro-Tyr-Glu-Gly-Thr-Gln-
Thr-Ala-Lys-Leu-Lys-Val-Thr-Lys-Gly-Gly-Pro-Leu-
Pro-Phe-Ala-Trp-Asp-Ile-Leu-Ser-Pro-Gln-Phe-Met-
Tyr-Gly-Ser-Lys-Ala-Tyr-Val-Lys-His-Pro-Ala-Asp-
Ile-Pro-Asp-Tyr-Leu-Lys-Leu-Ser-Phe-Pro-Glu-Gly-
Phe-Lys-Trp-Glu-Arg-Val-Met-Asn-Phe-Glu-Asp-Gly-
Gly-Val-Val-Thr-Val-Thr-Gln-Asp-Ser-Ser-Leu-Gln-
Asp-Gly-Glu-Phe-Ile-Tyr-Lys-Val-Lys-Leu-Arg-Gly-
Thr-Asn-Phe-Pro-Ser-Asp-Gly-Pro-Val-Met-Gln-Lys-
Lys-Thr-Met-Gly-Trp-Glu-Ala-Ser-Ser-Glu-Arg-Met-

-continued

Tyr-Pro-Glu-Asp-Gly-Ala-Leu-Lys-Gly-Glu-Ile-Lys-
Gln-Arg-Leu-Lys-Leu-Lys-Asp-Gly-Gly-His-Tyr-Asp-
Ala-Glu-Val-Lys-Thr-Thr-Tyr-Lys-Ala-Lys-Lys-Pro-
Val-Gln-Leu-Pro-Gly-Ala-Tyr-Asn-Val-Asn-Ile-Lys-
Leu-Asp-Ile-Thr-Ser-His-Asn-Glu-Asp-Tyr-Thr-Ile-
Val-Glu-Gln-Tyr-Glu-Arg-Ala-Glu-Gly-Arg-His-Ser-
Thr-Gly-Gly-Met-Asp-Glu-Leu-Tyr-Lys-[237]*Gly-Asp-*
*Glu-Val-Asp-Giu-Asp-Glu-Gly-*[246]Ala-Arg-Thr-Val-
Cys-Tyr-Ala-Ala-His-Val-Glu-Gly-Ile-Gly-Trp-Gln-
Gly-Ala-Val-Cys-Asp-Gly-Ala-Val-Ala-Gly-Thr-Thr-
Gly-Gln-Ser-Arg-Arg-Met-Glu-Ala-Ala-Val-1le-Ala-
Thr-Ser-Gly-Thr-Gly-Gly-Val-Cys-Ala-Asn-Ala-His-
Leu-Ala-Asp-Ile-Gly-Trp-Gln-Gly-Trp-Ala-Cys-Ala-
Ala-Asp-Gly-Lys-Ala-Val-Thr-Val-Gly-Thr-Thr-Gly-
Gln-Ser-Arg-Arg-Met-Glu-Ala-Leu-Gly-Leu-Gln-Val-
Gly-Asn-Gly-Ser-Val-Ala-Ala-Gln-Ala-His-Val-Ala-
Asp-Tyr-Gly-Trp-Leu-Asn-Ala-Glu-Gly-Gly-Asn-Pro-
Val-Tyr-Val-Gly-Thr-Thr-Gly-Gln-Ser-Arg-Arg-Met-
Glu-Ala-Val-Arg-Ile-Trp-Val-Leu-Glu-[379]His-His-
His-His-His-His

The SHA homologues having strong binding affinity to L-rhamnose or D-galactose are encompassed in this disclosure. These SHA homologues can be identified by their carbohydrate-binding properties, e.g., by using the commercially available Glycan Array 100 slides or other similar assays. Optionally, these SHA homologues can be further modified by substituting, deleting, or adding one or more amino acid residues to SEQ ID NO: 25. The modified SHA homologues may be tested for binding affinity to L-rhamnose and/or D-galactose to select the SHA homologues having similar or even improved binding affinity. Both SHA homologues without modification and the modified SHA homologues can be used for developing the GFP-SHA fusion proteins described above.

In some embodiments, SHA, the homologues or fragments of SHA can be labeled by a fluorescein or a derivative thereof such as FITC for easy detection. The fluorescein labeling has minimal impact on the binding activities of SHA or the homologue or fragment thereof.

In some embodiments, labeled or unlabeled SHA, SHA homologues or SHA fragments, and fusion proteins comprising a fluorescent protein and SHA or a homologue or fragment thereof disclosed herein, specifically bind to D-galactose and glycans containing Gal-α-1-3. In some embodiments, labeled or unlabeled SHA, SHA homologues or SHA fragments, and fusion proteins comprising a fluorescent protein and SHA or a homologue or fragment thereof disclosed herein, specifically bind to β-Gal-; α-Rha-; Gal-α-1,3-Gal-β-1,3-GlcNAc-β-; Gal-α-1,3-Gal-β-1,4-Glc-β-; Gal-α-1,4-Gal-β-1,3-GlcNAc-β-; Gal-α-1,3-(Fuc-α-1,2)-Gal-β- (for example, Blood B antigen trisaccharide); Gal-α-1,3-(Fuc-α-1,2)-Gal-β-1,4-Glc-β- (for example, Blood B antigen tetrasaccharide); or Gal-α-1,3-Gal-β-. In some embodiments, labeled or unlabeled SHA, SHA homologues or SHA fragments, and fusion proteins comprising a fluorescent protein and SHA or a homologue or fragment thereof disclosed herein, specifically bind to Gal-α-1,4-Gal-β-1,4-Glc-β-; GalNAc-β-1,3-Gal-β-1,4-Glc-β-; or Gal-α-1,4-Gal-β-1,4-GlcNAc-β-. In some embodiments, labeled or unlabeled SHA, SHA homologues or SHA fragments, and fusion proteins comprising a fluorescent protein and SHA or a homologue or fragment thereof disclosed herein, specifically bind to a carbohydrate terminating in or to a polysaccharide having one or more branches terminating in β-Gal-; α-Rha-; Gal-α-1,3-Gal-β-1,3-GlcNAc-β-; Gal-α-1,3-Gal-β-1,4-Glc-β-; Gal-α-1,4-Gal-β-1,3-GlcNAc-β-; Gal-α-1,3-(Fuc-α-1,2)-Gal-β-; Gal-α-1,3-(Fuc-α-1,2)-Gal-β-1,4-Glc-β-; Gal-α-1,3-Gal-β-, Gal-α-1,4-Gal-β-1,4-Glc-β-; GalNAc-β-1,3-Gal-β-1,4-Glc-β-; or Gal-α-1,4-Gal-β-1,4-GlcNAc-β-. In some embodiments, the fluorescent proteins include GFP and mCherry1. In some embodiments, the fluorescein or a derivative thereof includes FITC.

This disclosure demonstrates that archived SHA produced by S. sp. 27S5 and purified 40 years ago remained intact and maintained its carbohydrate-binding and hemagglutination (data not shown) activities, and that the molecular mass and primary structure of the archived SHA were successfully determined using modern mass spectrometric/proteomic strategies. The amino acid sequence of SHA was partially determined by Edman degradation methods in the 1970s, as described in the thesis of YFY(7). That study found redundancy in the N-terminal amino acid sequences of BrCN-cleaved SHA peptides, which was reasoned to be due to the presence of microheterogeneity in the purified protein. The primary structure disclosed herein clearly reveals that the difficulty of sequencing SHA in the 1970s was due to the three homologous SHA domains, which occupy 70% of the SHA molecule. It is fortuitous that the putative SHA gene of *S. lavendulae* was found in the *Streptomyces* genome database, which was expanded within two months after this protein was first revisited after 40 years. Consequently, the primary structure of SHA was revealed at last.

FTICR-MS revealed an average molecular mass of 13,314.67 Da and the presence of a covalently attached hexose in ~25% of the SHA molecules. The MS results suggest that hexose may be a component of SHA. Glycation of Lys in macromolecules, including hemoglobin, serum albumin, crystalline, and collagens, has been well studied (12-14). Given that the original SHA was obtained from a culture medium containing 2% D-fructose, it is possible that D-fructose was non-enzymatically attached to ε-amino groups of Lys. SHA was exposed to a high concentration of D-galactose after the original affinity purification, and significant amounts of D-galactose were found remaining in the archived SHA sample. Thus, it is also possible that D-galactose present in the SHA solution may have caused such a covalent linkage. Alternatively, it is possible that the hexose was added post-translationally by *Streptomyces*. However, the mass spectrometric data indicated multiple hexose-modified residues and not a single defined site (data not shown), hinting the presence of an inhomogeneous chemical reaction rather than a well-defined in vivo posttranslational modification.

The 131-amino acid primary structure of SHA was solved by showing that peptides derived from SHA aligned to the C-terminal two-thirds of the putative protein from *S. lavendulae* with >99% identity. Close comparison of peptides derived from SHA and the SHA domain of the putative protein revealed a single amino acid substitution at the SHA-equivalent position 108 in the putative protein, from E to A. Recombinant SHA(A108E) showed the same carbohydrate-binding specificity and similar affinity for L-rhamnose as archived SHA. These results confirmed that SHA is identical to the N-terminally truncated hypothetical protein in the genome of *S. lavendulae*, except that, in the putative protein, E in SHA-position 108 is substituted by A. The SHA(A108E) gene was used to express SHA proteins in different forms, including GFP-SHA. After the confirmation of L-rhamnose and D-galactose glycan specificity of the SHA(A108E) protein, this protein was designated as rSHA.

As the working examples demonstrate, SHA and eleven hypothetical protein homologues have three ChW-like SHA domains. To date, ChW domains have been exclusively found in the *C. acetobutylicum* species. The three ChW-like domains identified in SHA and its homologues represent additional examples for non-*C. acetobutylicum* proteins containing ChW domain repeats. The ChW domain is 45-47 amino acids long, and features an absolutely conserved tryptophan and high contents of hydrophobic and small amino acids. SHA homologues contain five conserved tryptophan residues, four of which are located in the three ChW-like SHA domains. Like the three SHA domains in SHA, the ChW domains cluster into groups of threes, which suggests they function as a triplet (10). Although carbohydrate recognition functions have been suggested (9), no conclusive study has been published as to the role of ChW domains.

The identified tryptophan residues may be involved in the binding function of SHA. It was previously reported that the circular dichroism (CD) spectrum of SHA strongly resembled that of poly(L-tryptophan), and speculated that tryptophan side chains contributed to a positive CD band at 226 nm (3). It was also suggested a potential involvement of tryptophan residues in L-rhamnose binding to SHA (4). Those conclusions were based on solvent-perturbation studies, which demonstrated that the number of solvent-exposed Trp (or average extent of exposure) was two in the absence of L-rhamnose, and three in the presence of L-rhamnose. This suggested that one tryptophan residue appears outside as a result of SHA binding to this sugar. Oxidation of two tryptophan residues with N-bromosuccinimide led to complete loss of its carbohydrate-binding activity, which also indicated that these tryptophan residues are important for retaining this activity (4). Using NMR, the current study confirmed the involvement of tryptophans in the binding of SHA to L-rhamnose. In analogy, another L-rhamnose-specific protein, α-L-rhamosidase of *S. avermitilis* has three tryptophan residues binding to L-rhamnose via hydrophobic interaction to the pyranose ring of the sugar (15).

The above-mentioned structural information is helpful for understanding specificity and affinity of SHA. It is important to carry out extensive binding assays of SHA against a variety of glycans. In this study, the specific binding of both archived SHA and rSHA was compared side by side, using the Glycan Array 100, and at two concentrations of SHA in the absence and presence of L-rhamnose. Although semi-quantitative, the results clearly revealed the following: (1) SHA bound to D-galactose and glycans containing Gal-α-1-3, which is the key signature of blood type B specificity, as well as L-rhamnose; (2) SHA bound to L-rhamnose with the highest affinity among glycans tested, as evidenced by the fact that the binding to L-rhamnose was still observed when other positive binding signals were abolished in the presence of 0.2M L-rhamnose; (3) SHA and rSHA showed the same glycan specificity profile, suggesting that rSHA represents the authentic SHA. These results are consistent with those previously published (2-4), confirming the blood type B and L-rhamnose specific nature of SHA. Gum arabic has been effectively used to purify SHA and SHA fusion proteins in the past and this study. As previously reported (2), hemagglutination of type B-erythrocytes by SHA was inhibited in the presence of plant-originated galactomannans, with guar gum>locust bean gum>gum arabic. The glycan structure resembling guar gum, locust bean gum, and gum arabic remains to be determined. These galactomannans are used in foods as stabilizers, and it is interesting to note that in the clinical setting, fungal galactomannan is used as a biomarker for invasive pulmonary aspergillosis, a life-threatening infection mainly affecting immunocompromised patients (16).

Although microbial lectins with similar characteristics to SHA have not been reported, significant data on L-rhamnose binding lectins (RBLs) from fish eggs are available (17-21). Interestingly, RBLs from a number of different fish species are composed of two or three domains consisting of approximately 100 amino acids, which are known as carbohydrate-recognition domains (RBL CRDs) (22,23). A lectin purified from sea urchin (*Anthocidaris crassispina*) eggs (SUEL) was reported to contain a galactose-binding lectin domain (24), but was later shown to bind to L-rhamnose preferentially, which seems reasonable given that L-rhamnose and D-galactose share the same hydroxyl group orientation at C2 and C4 of the pyranose ring structure (22,23). The RBL CRD, also called SUEL-type lectin domain, is composed of eight highly conserved half-Cys and several other conserved segments, e.g., YGA in the N-terminal and DP and K in the C-terminal domain (22). However, RBL CRD shows no homology to SHA domains, due to its domain size, which is over three times longer than the SHA domain; the absence of tryptophan, which is the signature of SHA domains; and its heavily disulfide-linked domain structure.

The functions of L-rhamnose-specific lectins are of particular interest. One suggested physiological role of fish egg lectins is as a defense mechanism against pathogenic bacteria (17). Rhamnose-binding lectins from salmon and trout are involved in innate immunity and recognition of lipopolysaccharides (LPS) or lipoteichoic acid (LTA), respectively, on the cell surface of bacteria (20,25). In contrast to animal lectins, lectins produced by microorganisms have different functions. Bacterial surface agglutinins with mannose specificity play roles in cell-cell interactions, as well as in microbial pathogenicity (26). The related functions of SHA are expected to include interactions with outside cells, such as attaching to neighboring plants and surrounding microorganisms, in addition to potential defense mechanisms. The closest SHA homologue was found in the *S. lavendulae* genome encoding a putative protein. If expressed by *Streptomyces*, this enzyme would be expected to catalyze the N- or O-deacetylation of acetylated sugars on the membranes of Gram-positive bacteria. However, it is not likely that SHA has such deacetylation activities, as SHA does not seem to recognize N-acetylated carbohydrates, as seen in the glycan array results.

The comparison of SHA to genomically-derived hypothetical proteins revealed the intriguing observation that the SHA-homologous domains of all eleven hypothetical proteins are localized in the C-terminal regions of the larger ORFs. Under the culturing conditions described (3), expression of the SHA-homologous proteins encoded by the genomes of *S. lavendulae* and S. sp. Mg1 was not observed (data not shown). In contrast, when the original study was performed in the 1970s, three HA activity-positive strains were identified from the 333 Actinomycetales culture supernatants screened (1). During the original screening, culture supernatants were serially diluted and incubated with blood type A, B, O, or AB erythrocyte suspensions. Supernatants that showed HA activity at 4- or 8-fold dilutions on titer plates were considered to be substantially positive; this included S. sp. 27S5 (1). SHA was purified from culture supernatants of S. sp. 27S5 by gum arabic affinity chromatography (3). It is possible that SHA could have been expressed as a precursor protein with an unknown N-terminal sequence, a signal sequence, and a protease-processing site, so that SHA molecules could be found in the culture broth, as observed 40 years ago.

As disclosed herein, the recombinant GFP-SHA binds to *L. casei* Shirota cells. Additional bacteria and fungi can be screened to identify microorganisms that interact with SHA. A similar approach was reported for a recombinant horseshoe crab plasma lectin that recognizes specific pathogen-associated molecular patterns of bacteria through L-rhamnose (27).

The SHA protein and homologues thereof, as well as fusion proteins of GFP and an SHA protein, an SHA homologue, or a functional fragment thereof (GFP-SHA and mCherry1-SHA fusion proteins) have a variety of novel uses in detecting the presence of certain microorganisms or cancer or tumor cells, diagnosing certain microbial infections or certain types of cancer or tumor, and detecting or imaging the location of microbial infections, or cancer or tumor, e.g., by PET scanning. Ideally, the fusion proteins are soluble, non-aggregating and stable for an extended period of time. The fusion proteins also retain the binding activity of SHA, a homologue or fragment thereof. The fusion proteins can bind well to the gum-Arabic carbohydrate column material and can be eluted with L-rhamnose or D-galactose.

For example, various bacteria or fungi expressing dTDP-4-dehydrorhamnose reductase gene (rmlD) may be detected in vitro by contacting the bacteria or fungi with a GFP-SHA or mCherry1-SHA fusion protein disclosed herein and monitoring the presence or change of fluorescence. In some embodiments, the bacterial or fungal cell expresses a carbohydrate containing L-rhamnose or D-galactose and display the carbohydrate on the surface of the cell. The GFP-SHA and mCherry1-SHA fusion proteins can detect the presence of such microorganisms in various liquid samples from a subject, e.g., a biopsy sample, a tissue sample, a bronchoalveolar lavage sample, a blood sample, and a urine sample. Alternatively, if the bacterial or fungal cell expresses a carbohydrate containing L-rhamnose or D-galactose but does not display the carbohydrate on the surface of the cell, the GFP-SHA and mCherry1-SHA fusion proteins can detect the presence of such microorganisms in fixed tissue samples, e.g., paraffin-fixed or formalin-fixed and paraffin-embedded tissue samples.

Similarly, various cancer or tumor cells expressing tumor-specific carbohydrates can be detected using the GFP-SHA and mCherry1-SHA fusion proteins disclosed herein. Such carbohydrates contain or terminate in beta-Galactose-(β-Gal-); Gal-α-1,3-; Gal-β-1,3-GlcNAc-β-; Gal-α-1,3-Gal-β-1,4-Glc-β-; Gal-α-1,4-Gal-β-1,3-GlcNAc-β-; Gal-α-1,3-(Fuc-α-1,2)-Gal-β-; Gal-α-1,3-(Fuc-α-1,2)-Gal-β-1,4-Glc-β-; Gal-α-1,3-Gal-β-; Gal-α-1,4-Gal-β-1,4-Glc-β-; GalNAc-β-1,3-; Gal-β-1,4-Glc-β-; or Gal-α-1,4-Gal-β-1,4-GlcNAc-β-. In some embodiments, the core structures of the Thomsen Friedenreich and mucin antigens terminate in galactose and therefore, can be detected by the GFP-SHA and mCherry1-SHA fusion proteins disclosed herein. The GFP-SHA and mCherry1-SHA fusion proteins can detect the presence of such cancer or tumor cells in various liquid samples from a subject, e.g., a biopsy sample, a tissue sample, a bronchoalveolar lavage sample, a blood sample, and a urine sample. Alternatively, if the cancer or tumor cell expresses a carbohydrate capable of specifically binding to SHA, a homologue thereof, or a fragment of the SHA or a homologue thereof disclosed herein but does not display the carbohydrate on the surface of the cell, the GFP-SHA and mCherry1-SHA fusion proteins can detect the presence of such a cancer or tumor cell in fixed tissue samples, e.g., paraffin-fixed or formalin-fixed and paraffin-embedded tissue samples. In some embodiments, the cancer is colon cancer.

The GFP-SHA and mCherry1-SHA fusion proteins can be used for diagnosis of various microbial infections caused by one or more microorganisms expressing a carbohydrate containing L-rhamnose or D-galactose or various cancers or tumors expressing tumor-specific carbohydrates capable of specifically binding to SHA, a homologue thereof, or a fragment of the SHA or a homologue thereof disclosed herein. The method entails the step of contacting a sample obtained from a subject suffering from a microbial infection or a cancer or tumor with a GFP-SHA fusion protein or an mCherry1-SHA fusion protein, and determining the fluorescence level in the sample, wherein the presence of the fluorescence indicating the condition of the microbial infection or cancer or tumor. In some embodiments, the method further entails the step of contacting a sample obtained from a negative control subject, such as a healthy subject or the subject before the microbial infection or without cancer or tumor, with a GFP-SHA or mCherry1-SHA fusion protein, and comparing the fluorescence levels of the sample of the negative control subject with the sample of the subject suffering from the microbial infection or cancer or tumor, wherein the difference in the fluorescence levels indicating the microbial infection or presence of cancer or tumor. Alternatively, the fluorescence level of a negative control subject can be established by an average or median fluorescence level of a population of healthy subjects who do not suffer from the microbial infection or cancer or tumor. In some embodiments, the cancer is colon cancer.

In a related aspect, this disclosure relates to a method of determining the prognosis of treating a microbial infection caused by one or more microorganisms expressing a carbohydrate containing L-rhamnose or D-galactose or a cancer or tumor expressing a carbohydrate tumor antigen capable of specifically binding to SHA, a homologue thereof, or a fragment of the SHA or a homologue thereof disclosed herein. The method entails the step of contacting a sample obtained from a subject suffering from a microbial infection or a cancer or tumor with a GFP-SHA or mCherry1-SHA fusion protein to determine the fluorescence level, treating the subject suffering from a microbial infection with one or more antimicrobial agents or the subject suffering from a cancer or tumor with one or more cancer therapies, contacting a sample obtained from the subject after the treatment with a GFP-SHA or mCherry1-SHA fusion protein to determine the fluorescence level, and comparing the fluorescence levels before and after the treatment to determine the prognosis of the treatment. The method can further comprise administering to the subject an alternative antimicrobial agent or cancer therapy or an additional amount of the antimicrobial agent or cancer therapy if a desired prognosis is not achieved. In some embodiments, the cancer is colon cancer.

Infections caused by various microorganisms or certain types of cancers or tumors can be detected based on the specific binding of the GFP-SHA or mCherry1-SHA fusion proteins disclosed herein with the carbohydrate containing L-rhamnose or D-galactose displayed on the surface of the microorganisms or the carbohydrate tumor antigen capable of specifically binding to SHA, a homologue thereof, or a fragment of the SHA or a homologue thereof disclosed herein. As demonstrated in the working examples, the GFP-SHA or mCherry1-SHA fusion proteins and fluorescein labeled SHA disclosed herein can specifically bind to β-Gal-; α-Rha-; Gal-α-1,3-Gal-β-1,3-GlcNAc-β-; Gal-α-1,3-Gal-β-1,4-Glc-β-; Gal-α-1,4-Ga-β-1,3-GlcNAc-β-; Gal-α-1,3-(Fuc-α-1,2)-Gal-β-; Gal-α-1,3-(Fuc-α-1,2)-Gal-β-1,4-Glc-β-; Gal-α-1,3-Gal-β-, Gal-α-1,4-Gal-β-1,4-Glc-β-; GalNAc-β-1,3-Gal-β-1,4-Glc-β-; or Gal-α-1,4-Gal-β-1,4-GlcNAc-β-. The GFP-SHA fusion proteins can be used to detect microbial infections caused by a microorganism expressing a carbohydrate terminating in or otherwise exposing the aforementioned monosaccharides or oligosaccharides. Alternatively, the GFP-SHA and mCherry1-SHA fusion proteins can be used to detect cancer or tumor cells expressing a carbohydrate tumor antigen terminating in or otherwise exposing the aforementioned monosaccharides or oligosaccharides. In some embodiments, the cancer is colon cancer.

In yet another related aspect, disclosed herein is a method of imaging a local microbial infection site caused by a microorganism expressing a carbohydrate containing L-rhamnose or D-galactose. Alternatively, the method of imaging a tumor site, where the tumor cell expresses a tumor-specific antigen including a carbohydrate capable of specifically binding to SHA, a homologue thereof, or a fragment of the SHA or a homologue thereof disclosed herein, can be performed in a similar way. In some embodiments, the cancer is colon cancer. A GFP-SHA or mCherry1-SHA fusion protein, labeled or unlabeled SHA protein or a homologue thereof, or a functional fragment of the SHA protein or a homologue thereof, can be labeled with a PET isotope to produce a PET probe. The method entails the step of administering to a subject suffering from a microbial infection or a cancer or tumor the PET probe, and performing a PET scanning of the subject to image the location of the microbial infection or cancer or tumor, or to detect the location of the PET probe, thereby determining the location of the microbial infection or the cancer or tumor. In some embodiments, the PET probe is administered to the subject by intravenous injection. In some embodiments, the PET probe is locally administered to the microbial infection site or the tumor site.

The selection and use of a suitable PET probe can be done based on the knowledge in the field (29). For example, the PET imaging can be performed using a DOTA-labeled GFP-SHA or mCherry1-SHA fusion protein. DOTA is a chelator (1,4,7,10-tetraazacyclododecane-1,4,7,10-tetraacetic acid) that is used to covalently attach PET imaging metal isotopes to proteins. For example, $^{68}$Ga or $^{64}$Cu can be used in this technique. There are many other PET metal isotopes that can be used and are compatible with DOTA chelation. Other labeling techniques also can be used, for example, non-metal PET isotopes including 124-Iodine, 18F, etc.

In some embodiments, the DOTA labeling is conducted via an attachment to amino acids such as lysine (via amino groups) or cysteines (via thiols). In some embodiments, the DOTA labeling is attached to one or more amino acids located in the SHA protein, a homologue thereof, or a functional fragment of the SHA protein or a homologue thereof. In some embodiments, the DOTA labeling is attached to one or more amino acids located in GFP or mCherry1 of a GFP-SHA or mCherry1-SHA fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Materials and Methods

Materials-*S. lavendulae* strain NCIB 6959/ATCC 14158 and HEK293S cells were purchased from ATCC (Manassas, Va.). S. sp. strain Mg1 was a kind gift from Dr. Paul Straight of Texas A&M University (6). *E. coli* C41(DE3) and E. Clone® were from Lucigen (Middleton, Wis.). Gum arabic was purchased from Sigma-Aldrich (St. Louis, Mo.). MS-grade Trypsin, LysC, ArgC, V8 protease, and pepsin were from Promega (Madison, Wis.). Chymotrypsin was from Worthington Biochemical (Lakewood, N.J.). pET32b and pcDNA3.1 vectors were from Merck Millipore (Billerica, Mass.) and Thermo Fisher Scientific (Waltham, Mass.), respectively.

Purification and characterization-SHA was purified forty years ago as described (3) and kept frozen at −80° C. The purity and quality of the archived SHA were determined using SDS-PAGE. The N-terminal amino acid sequence of SHA was determined using Edman degradation performed on the Procise 494HT Protein Sequencing System (Applied Biosystems, Thermo Fisher Scientific).

Specific binding of SHA to gum arabic gels-Gum arabic gels were prepared according to published methods (3). The archived SHA as well as recombinant SHA proteins were applied to the gum arabic gel column. After washing the column, SHAs were eluted with either 1 M D-galactose in the presence of 1 M NaCl as described (3), or 0.2 M L-rhamnose in the presence of 1 M NaCl.

NMR titration study-NMR analysis was performed using a DRX-500 spectrometer equipped with a cryogenic TXI probe (Bruker BioSpin, Billerica, Mass.). The probe temperature was set to 298 K. Archived SHA (0.1 mg) was dissolved in 500 μl of 20 mM sodium phosphate buffer, pH 6.5 ($H_2O$:$D_2O$=9:1). L-rhamnose solution was added to the SHA solution at molar ratios from 1:0 to 1:5 (SHA:L-rhamnose). Data processing and analysis were performed using XWIN-NMR (ver. 3.5, Bruker BioSpin). NMR spectra were displayed with XWIN-PLOT (ver. 3.5, Bruker BioSpin).

Mass Spectrometry—To determine molecular mass, the intact archived SHA was analyzed using electrospray ionization (ESI) Fourier Transform Ion Cyclotron Resonance (FTICR)-MS on a Thermo LTQ FTICR (Thermo Fisher) at ~500,000 resolution.

To determine the amino acid sequence of SHA, overlapping SHA peptides were obtained by performing separate enzymatic digestions with trypsin, chymotrypsin, LysC, ArgC, V8 protease, and pepsin, and analyzed by LC-MS on an Orbitrap Fusion Tribrid Mass Spectrometer (Thermo Fisher Scientific, Waltham Mass.), as well as by MALDI-MS on a SimulTof Combo 200 instrument (SimulTOF Systems, Virgin Instruments, Marlborough, Mass.). MS and MS/MS collision-induced dissociation (CID) fragmentation data from these peptides were analyzed with Xcalibur software (Thermo Fisher Scientific) and with PEAKS Studio software (Bioinformatics Solutions Inc., Waterloo, Ontario, Canada).

SHA disulfide bond determination was made using MALDI-MS and high (120,000) resolution Thermo Orbitrap Fusion Tribrid Mass Spectrometer analysis of the intact protein and the digested protein, before and after reduction with 50 μM TCEP, pH 2.0, at 80° C. for 30 min.

Expression of an SHA homologous recombinant protein—the SHA homologous domain of the putative protein from *S. lavendulae* was expressed, which showed the highest homology to SHA (>99% identity), as a recombinant protein. To develop this recombinant SHA homologue, a synthetic gene expressing a wild-type SHA of the putative protein and a mutant SHA gene with an A to E amino acid substitution at position 108 (A108E), were produced using *E. coli* codon-optimized overlapping oligo DNA primers, and cloned into pET32b (Table 1). The primer binding sites are illustrated in FIG. 1.

TABLE 1

| Primer Name | SEQ ID NO: | DNA Sequence |
|---|---|---|
| P1f | 1 | TGCGCGAACGCGCACCTGGCGGACATCGGTTGGCAGGGTTGGGCGTGCGCGGCGGACGGT |
| P2f | 2 | CGTATGGAAGCGGCGGTTATCGCGACCTCTGGTACCGGTGGTGTTTGCGCGAACGCGCAC |
| P3f | 3 | GTTTGCGACGGTGCGGTTGCGGGTACCACCGGTCAGTCTCGTCGTATGGAAGCGGCGGTT |
| P4f | 4 | GCGGCGCACGTTGAAGGTATCGGTTGGCAGGGTGCGGTTTGCGACGGTGCGGTTGCGGGT |
| 5af | 5 | AAAGAATTCGCGCCGGCGGCGCGTACCGTTTGCTACGCGGCGCACGTTGAAGGTATCGGT |
| P1r | 6 | TCCATACGACGAGACTGACCGGTGGTACCAACGGTAACCGCTTTACCGTCCGCCGCGCAC |
| P2r | 7 | GCCTGCGCCGCAACAGAACCGTTACCAACTTGCAGACCCAGCGCTTCCATACGACGAGAC |
| P3r | 8 | TTACCACCCGCCGCGTTCAGCCAACCGTAGTCCGCAACGTGCGCCTGCGCCGCAACAGAA |
| P4ar | 9 | CGACGGGACTGACCAGTAGTGCCAACGTAAACCGGGTTGCCACCCGCCGCGTTCAGCCAA |
| P5ar | 10 | TTTCTCGAGTTAAACCCAGATACGAACCGCTTCCATACGACGGGACTGACCAGTAGTGCC |

TABLE 1-continued

| Primer Name | SEQ ID NO: | DNA Sequence |
|---|---|---|
| PDSL A108Ef | 11 | GACTACGGTTGGCTGAACGCGGAAGGTGGCAACCCGGTTTACGTTGGC |
| PDSL A108Er | 12 | GCCAACGTAAACCGGGTTGCCACCTTCCGCGTTCAGCCAACCGTAGTC |

The recombinant wild-type SHA was expressed in *E. coli* C41(DE3) as a thioredoxin (Trx) fusion protein with His-tag. Trx-SHA was purified from *E. coli* cell pellets derived from a 2-L culture by solubilization and affinity purification on a Ni-NTA resin (Thermo Fisher Scientific). The purified wild-type SHA was digested with multiple enzyme combinations, as described above for SHA, to compare resulting peptides from both proteins.

Due to solubility issues various fusion proteins of the recombinant SHA were prepared and expressed in *E. coli*. Of those, a yeast SUMO(SMT3)-fusion protein was successfully purified for comparing carbohydrate-binding specificity with that of archived SHA. Briefly, SMT3-fused SHA(A108E) was prepared by insertion at the SMT3 and Ulp1 cleavage sites of pET32b/SHA(A108E). *E. Cloni*® (Lucigen) was transformed by pET32b/SMT3-SHA (A108E). SMT3-SHA(A108E) was purified using a His6-tag specific nickel-NTA column from transformed cells after solubilization with 5M urea/B-Per lysis buffer (Pierce), followed by refolding in the presence of 1 M galactose and 10 mM β-mercaptoethanol. SHA(A108E) was cleaved off from SMT3 bound to the column by incubating with UPL1. The resulting SHA(A108E) was purified by gum arabic gels. The authenticity of SHA(A108E) was confirmed by SDS-PAGE and glycan microarray analyses.

Glycan microarray analyses—Microarray analysis was performed according to the manufacturer recommendations using RayBio Glycan Array 100 (RayBiotech, Norcross Ga.) slides. Each slide contains four sub-microarrays printed with 100 synthetic glycans. Briefly, 200 μL of 0.1 mg/mL of both archived SHA and rSHA were dialyzed overnight at 4° C. against 1×PBS dialysis buffer to avoid contaminating samples with amines prior to biotinylation. Dialyzed samples were incubated with biotin-containing reaction solution at 22° C. for 30 min. Sub-arrays were blocked for 30 min at 22° C. After biotinylated SHA samples were diluted with 1×PBS, 400 μL of each sample was added to each sub-array. Slide #1 sub-arrays were incubated with 400 μL of 20 μg/mL (1×) or 2 μg/mL (0.1×) SHA, in the absence or presence of 0.2 M L-Rhamnose. Slide #2 sub-arrays were incubated with 400 μL of 20 μg/mL (1×) or 2 μg/mL of rSHA (0.1×), in the absence or presence of 0.2 M L-rhamnose. Slides were incubated for 16 h at 4° C. for highest intensities. Washing was performed according to the manufacturer's protocol, followed by incubation with Cy3 dye-conjugated streptavidin. The slides were incubated at 22° C. for 1 h with gentle shaking, then washed multiple times as recommended. The signals were visualized using an Agilent DNA microarray scanner (Model G2505C; Agilent, Santa Clara, Calif.) at 532 nm for Cy3. Data extraction and analysis was performed after subtraction of the background and normalization to the internal references provided by the manufacturer, using an ImageJ Protein Array Analyzer software (28).

Staining of *Lactobacillus casei* (Shirota) cells by fluorescently labeled SHA-Recombinant GFP-SHA was expressed by inserting the SHA(A108E) gene at the C-terminus of GFP in pET28/GFP, followed by transformation of *E. cloni* cells. GFP-SHA was purified from cell pellets collected from 4-L culture, after solubilization with 5 M urea/B-Per lysis buffer (Pierce), using a His6-tag specific nickel-NTA column, followed by refolding in the presence of 1 M galactose and 10 mM β-mercaptoethanol, and eluting with 400 mM imidazole. GFP-SHA was concentrated using Centricon YM10 centrifugal filters (Fisher Scientific) and purified by FPLC with Superdex 75G (GE Healthcare Life Science, Pittsburgh, Pa.).

*L. casei* Shirota cells were isolated from commercially available Yakult yogurt drink. The authenticity of *L. casei* Shirota was verified by Sanger sequencing of its 16S rRNA by showing 100% match to the reference sequence AB531131. Four hundred ml Difco™ Lactobacilli MRS Broth (Fisher Scientific) was inoculated with *L. casei* Shirota cells at a concentration of $10^6$ cells/mL. *L. casei* Shirota cells were grown for 16 h at 37° C., harvested by centrifugation, and washed three times with 1×PBS. Cells were re-suspended in 5 ml 70% ethanol and incubated at 22° C. for 30 min under continuous rotation. Cells were washed three times with 1×PBS, then re-suspended in 5 ml 1×PBS. Bacterial cells were blocked for non-specific binding with 3% BSA in PBS and NP-40 (0.5%) for 30 min, followed by 1 h incubation with 50 μM of GFP-SHA or GFP as a negative control. Cells were washed three times with 1×PBS and finally re-suspended in 1 mL PBS containing 10% glycerol. Bacteria cells were counter-stained with DAPI (3 μM) and examined using a Zeiss Observer II system (Carl Zeiss, Jena, Germany). Fluorescent images were analyzed using Image-Pro Plus and ZEISS ZEN software (Carl Zeiss, Jena, Germany).

Example 1: Preservation of Active SHA

Figure 2:
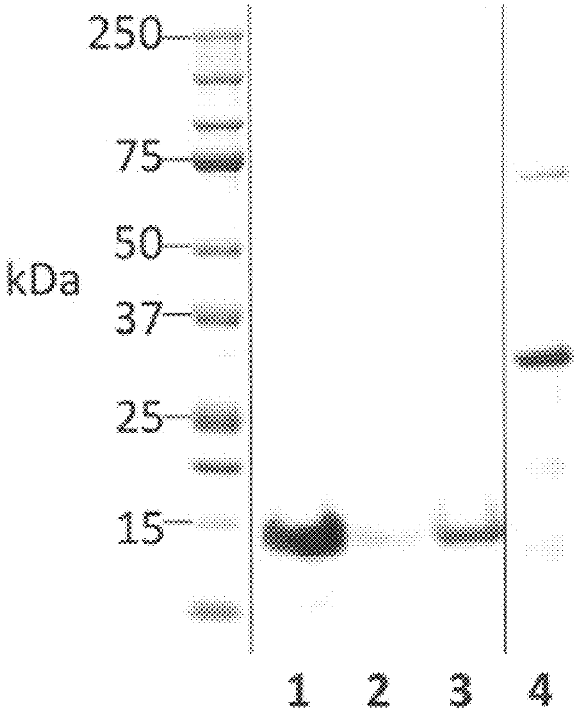
FIG. 2 demonstrates SDS-PAGE analysis of archived SHA and thioredoxin (Trx) fused-SHA. S. sp. 27S5-produced SHA and a recombinant SHA homologue, Trx-SHA, were separated by SDS-PAGE on a 5-12% gradient gel and visualized with Coomassie Blue stain. Archived SHA (lane 1) was applied to a gum arabic gel column from which SHA was eluted by 1 M D-galactose (lane 2) or 0.2 M L-rhamnose (lane 3) in the presence of 1 M NaCl. Recombinant SHA was expressed in *E. coli* as a Trx-fusion protein and purified (lane 4). Gel image was assembled from three sections of the same gel; omitted spaces are indicated by the vertical lines.

It was first confirmed that the SHA protein that was purified 40 years ago and archived in a frozen state, was intact, readily bound to a gum arabic affinity chromatography column, and specifically eluted with a competing monosaccharide D-galactose or L-rhamnose as shown in FIG. 2, lanes 1-3.

Figure 3:
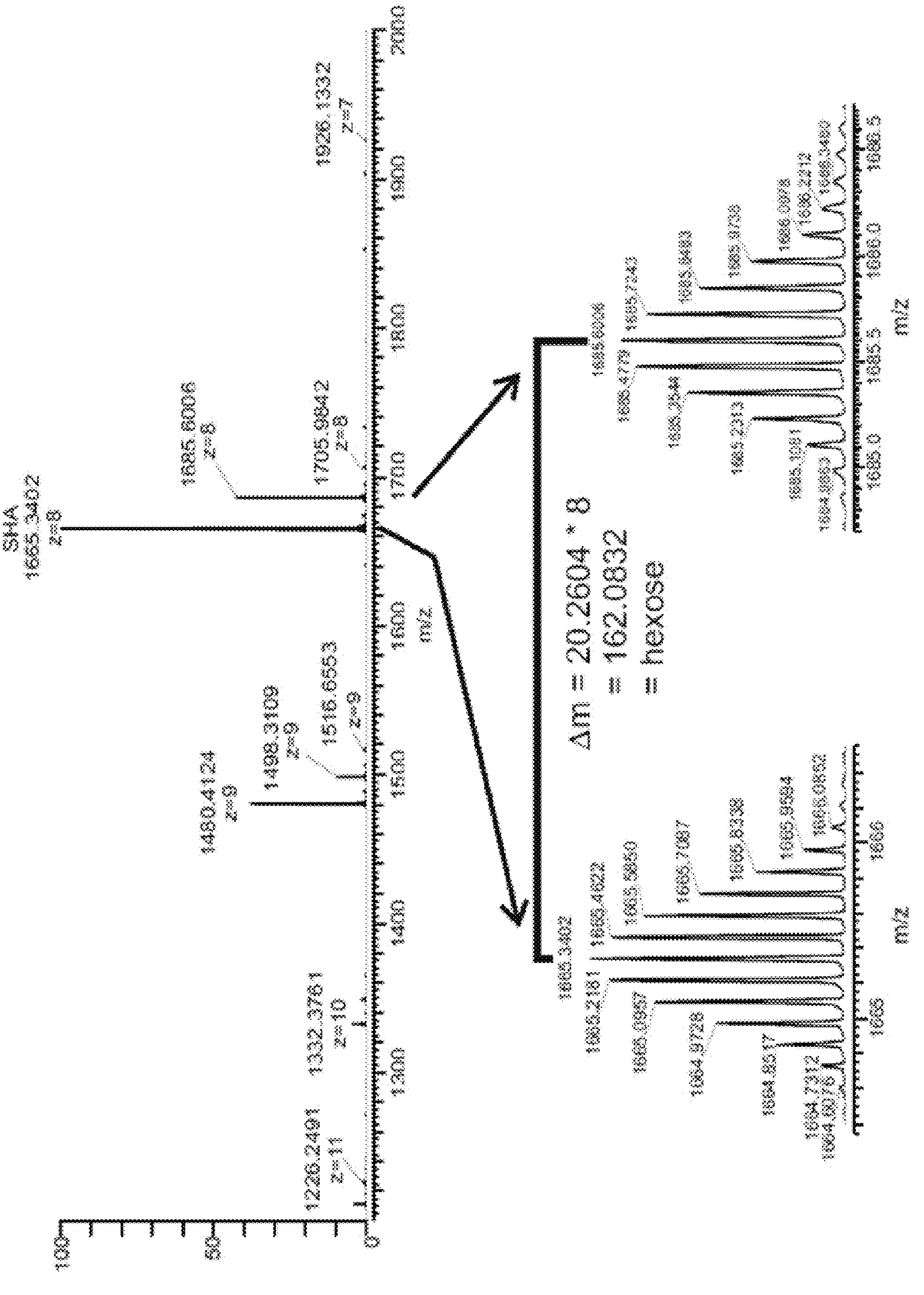
FIG. 3 demonstrates the determination of the molecular mass of SHA. Electrospray Ionization (ESI) Fourier Transform Ion Cyclotron Resonance (FTICR)-MS of archived, forty-year old SHA revealed an average molecular mass of 13,314.67 Da, a monoisotopic mass of 13,306.65 Da, and the presence of a covalently attached hexose in ~25% of the SHA molecules. The isotope distributions of the molecular SHA ions with a charge state of z=8 are magnified below the original spectrum.

Example 2: Determination of the Molecular Mass of SHA Using Mass Spectrometry The molecular mass of SHA was previously estimated to be approximately 11 kDa, based on various approaches, including gel filtration in the presence of 6 M guanidine hydrochloride, SDS-PAGE, and sedimentation equilibrium analysis (3). Electrospray ionization (ESI) Fourier Transform Ion Cyclotron Resonance (FTICR) MS was applied to determine the molecular mass of SHA more precisely. This high-resolution mass spectrometric technique revealed a precise average molecular mass of 13,314.67 Da, a monoisotopic mass of 13,306.65 Da, and the presence of a covalently attached hexose in ~25% of the SHA molecules (FIG. 3).

Example 3: Identification of SHA Homologues in *Streptomyces* Genomes

Figure 4:
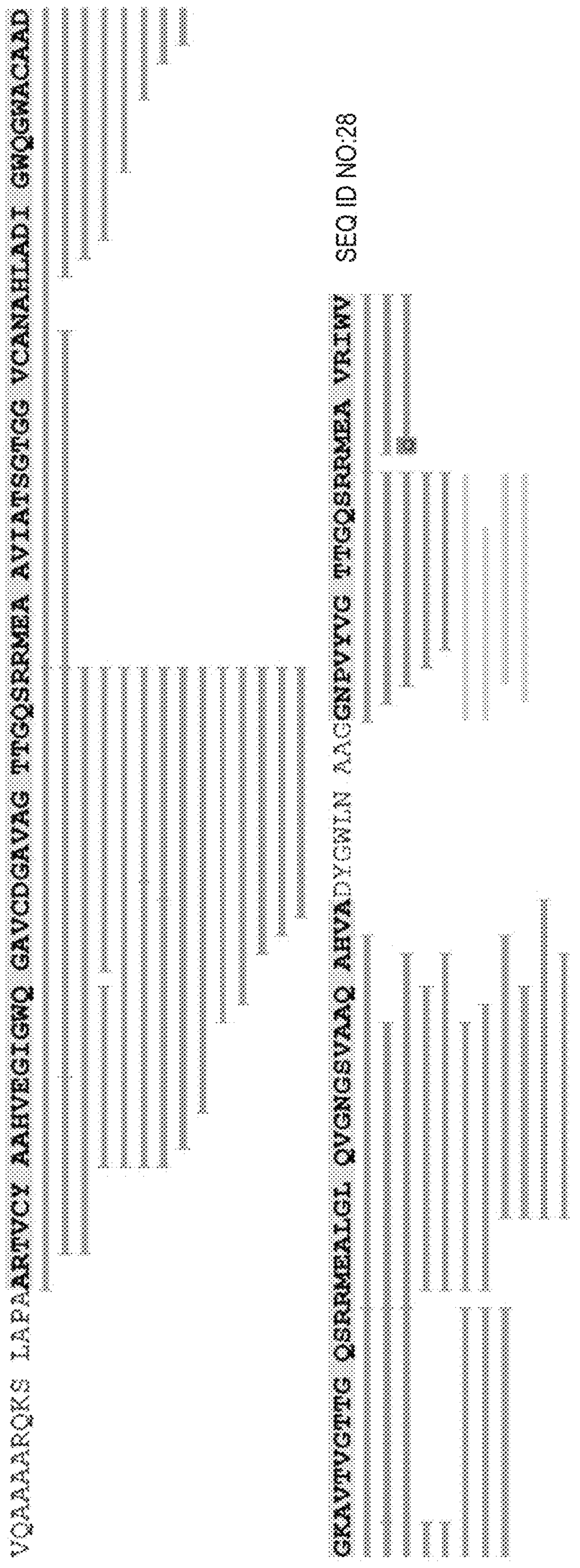
FIG. 4 demonstrates LC MS/MS data of SHA proteolysis products aligned with the deduced amino acid sequence from the homologous partial sequence of the putative polysaccharide deacetylase of *S. lavendulae* (PDSL, WP 051840348.1). Overlapping SHA peptides were generated by separate enzymatic digestions and analyzed by high resolution Orbitrap LC-MS. Blue lines indicate database matches, grey lines mark matches through de nova sequencing with PEAKS software, and red-boxed 0 indicates methionine oxidation.

To determine the sequence identity of SHA, bottom-up proteomics experiments were conducted. SHA was digested separately with several proteases to generate overlapping peptides. These peptides were then analyzed by liquid chromatography (LC) coupled with high-resolution multistage mass spectrometry (MS/MS). An initial database search was performed and revealed a closely matching SHA homologue in the genome of *Streptomyces* sp. Mg1 as a hypothetical protein (GenBank accession #EDX26679.1) (6); data not shown. More *Streptomyces* genome sequences became available later; subsequently, a more refined search led to the identification of a homologue in *S. lavendulae* with even better scores for MS/MS database matching. The digested SHA peptides aligned almost completely with the deduced C-terminal amino acid sequence of the putative polysaccharide deacetylase of *S. lavendulae* (Accession number WP_051840348.1; FIG. 4). SHA matched with the C-terminal 131 amino acids of the hypothetical 199-amino acid protein, except for a partial sequence stretch consisting of nine amino acids from SHA-position 101-109. However, the mass spectrometric data did not cover any sequence of the N-terminal portion of either the S. sp. Mg1 or *S. lavendulae* protein, comprising 74 and 68 amino acid residues, respectively.

Example 4: Determination of the N-Terminal Amino Acid Sequence of SHA

Previous amino acid sequencing of reduced and carboxymethylated SHA revealed the N-terminal amino acids to be AxTVCYAAxV (SEQ ID NO: 13) (7); x indicates an undetermined residue. To confirm these results and identify additional amino acids in the sequence, N-terminal sequencing of the archived SHA was performed. Approximately 30 amino acids were identified to be ARTVcYAAHVEGIGWQGAVcDGAVAxTtxQsRr (SEQ ID NO; 14) (lowercase letters indicate tentative identification). Together, the two independent N-terminal sequencing results strongly suggested that the N-terminal sequence of SHA was ARTVCY (SEQ ID NO: 15).

Example 5: Solution of the Primary Structure of SHA

Figure 5A:
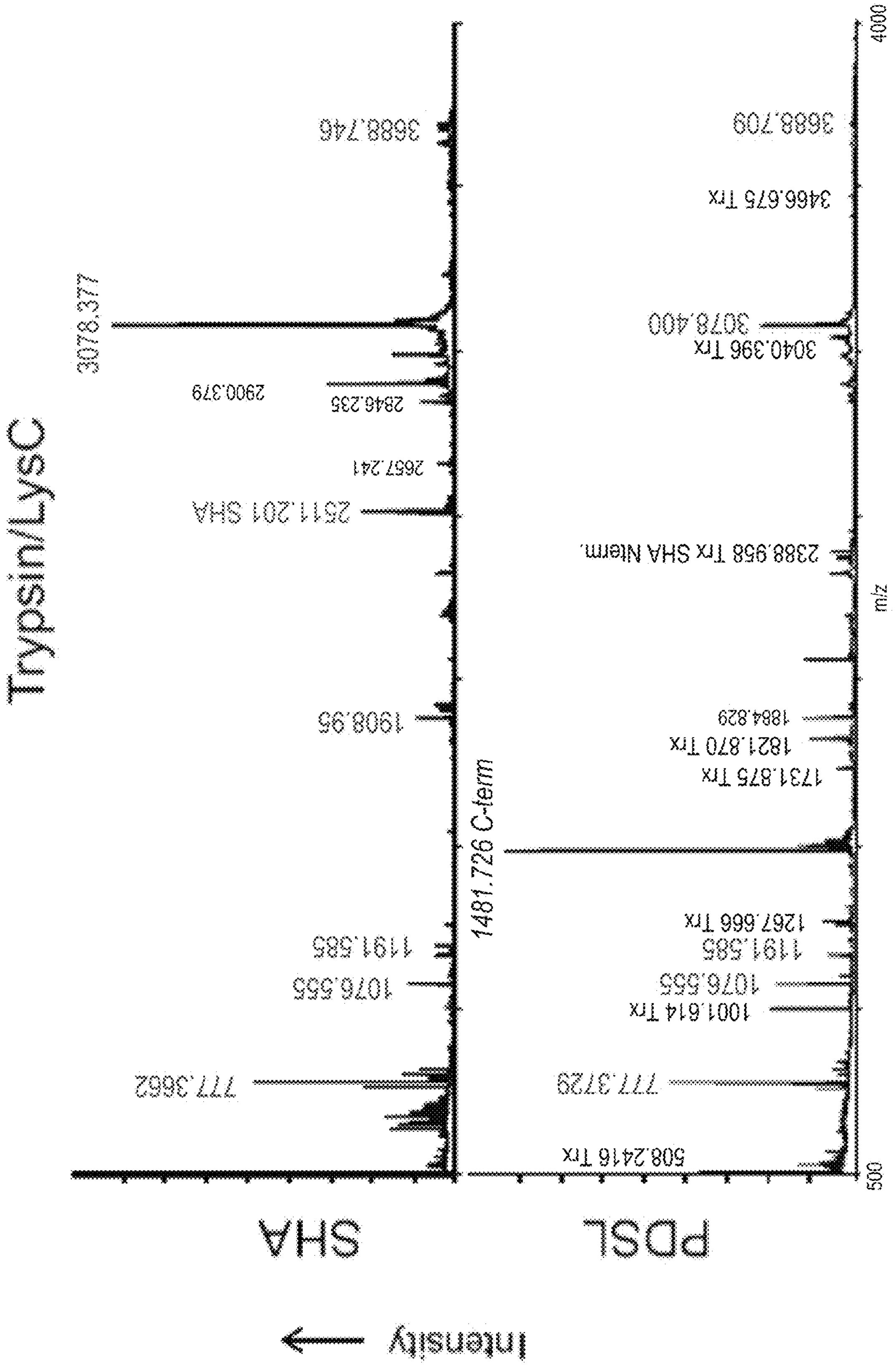
FIGS. 5A-5D show the primary structure of SHA.
Figure 5B:
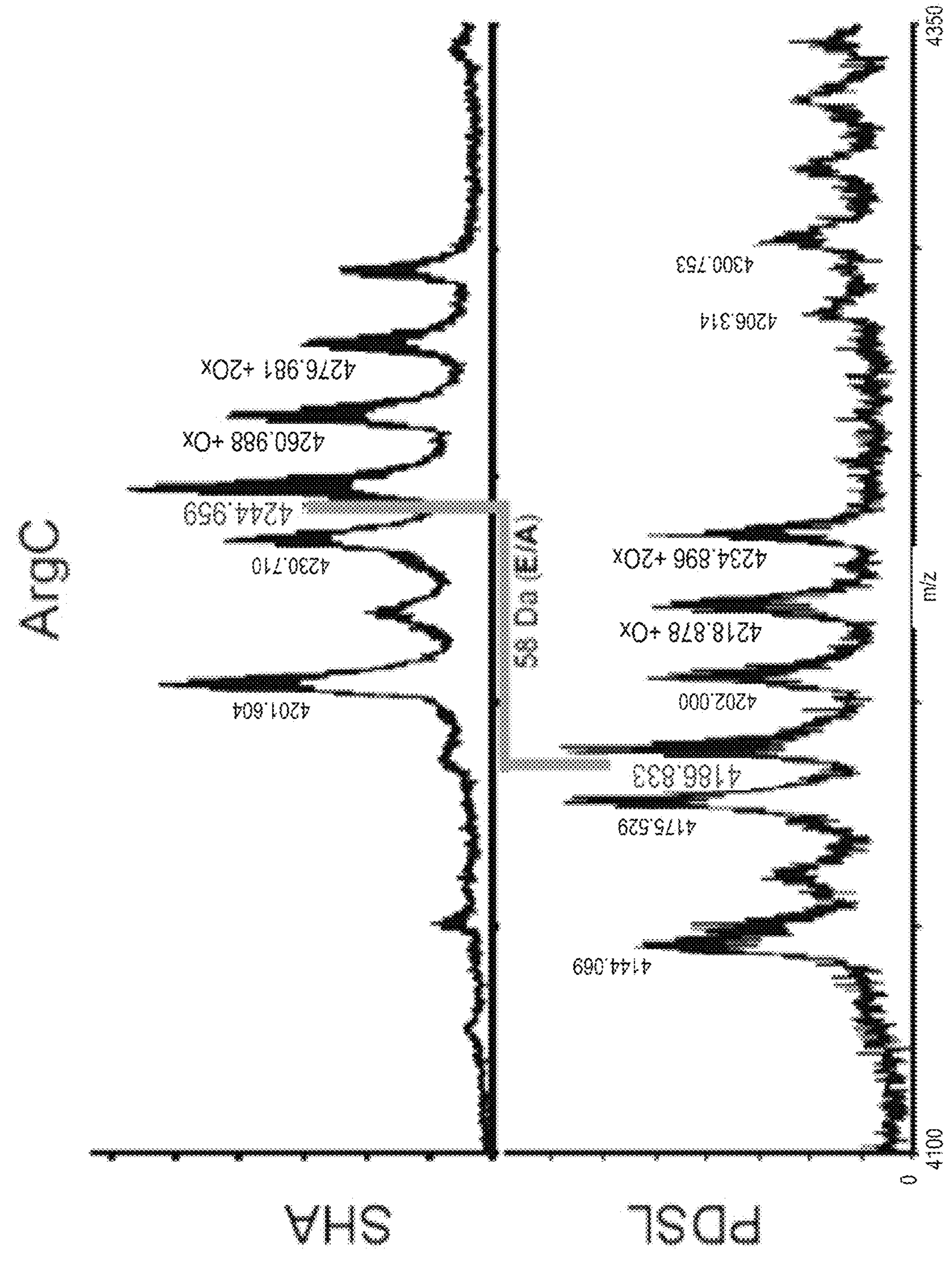

By considering the N-terminal sequencing information, the molecular mass of the intact SHA protein, and the database matching with digested peptides, the SHA sequence appeared to be almost identical to the C-terminal portion of the putative protein, residues 69-199. To identify how the amino acid sequences differ between SHA and the SHA domain of the putative protein, a recombinant thioredoxin (Trx)-SHA fusion protein was generated and peptide fingerprints of the recombinant SHA and SHA putative protein were compared. First, the homologous SHA domain from the putative protein was cloned into a PET32 vector to transform *E. coli*, from which the fusion protein was purified using Ni-NTA resin (FIG. 2, lane 4). Then the purified recombinant Trx-SHA fusion protein was digested using multiple enzymes to generate overlapping peptides for LC-MS and MALDI-MS analyses, as for SHA above. Finally, the LC-MS/MS data sets of the digested peptides from the recombinant SHA and its homologue SHA putative protein were compared. It was found that the sequence of the recombinant SHA differed from that of SHA putative protein by a single A108E change (FIGS. 5A and 5B). This was confirmed by calculating and comparing the molecular masses for the recombinant SHA and SHA putative protein as a 58-Da mass difference.

Figure 5C:
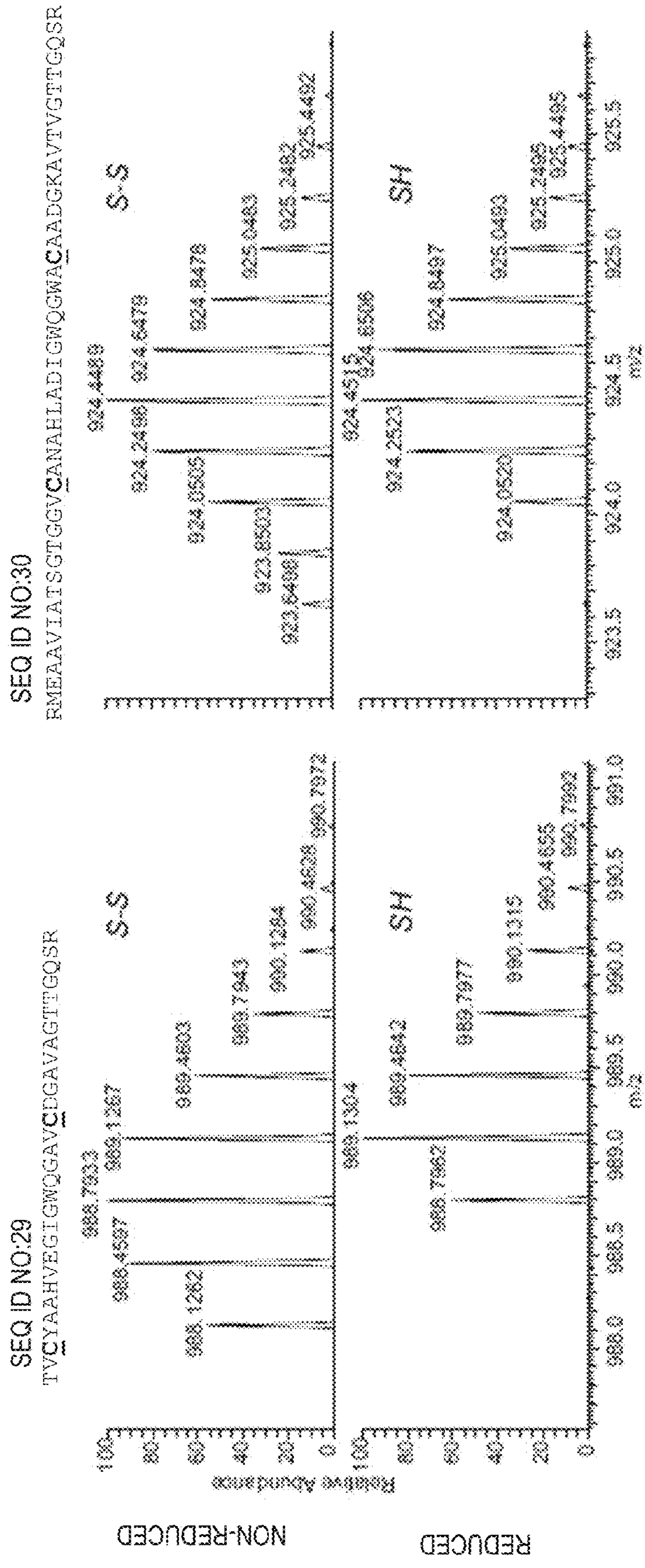
Figure 5D:
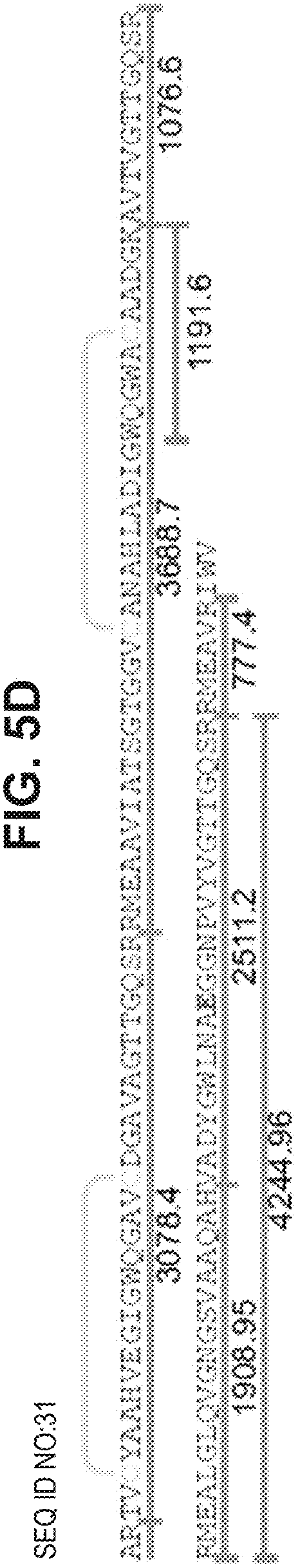

To determine disulfide bonds in SHA, endoproteinase ArgC was used to digest archived SHA, with or without reduction with tris(2-carboxyethyl) phosphine (TCEP), followed by high resolution Orbitrap LC-MS. Comparison of the spectra of two digested peptides before and after TCEP reduction showed a clear 2-Da mass difference (FIG. 5C). This indicates that SHA contains two consecutive disulfide bonds that connect cysteine residues C5 with C20 and C48 with C63, as illustrated in FIG. 5D. No other disulfide bond-connected peptides were detected. Taken together, these results allowed deduction of the primary structure of SHA (illustrated in FIG. 5D, and summarized in Tables 2 and 3, along with repetitive domain structures).

Table 2 demonstrates that three homologous SHA domains, consisting of 92 amino acids, form 70% of the total amino acids of SHA. The primary sequence of SHA is principally composed of three homologous SHA domains 1, 2, and 3, consisting of 29, 33, and 30 amino acids, respectively. Together, the three SHA domains comprise 92 amino acids, 70% of the total 131 amino acids in SHA. Underlining indicates the completely matched 11-amino acid sequences in these domains. Homology among the three SHA domains is shown in FIG. 81.

TABLE 2

| Location | Amino acid sequence | Number of residues | ChW-like domains |
|---|---|---|---|
| 1-7 | ARTVCYA (SEQ ID NO: 16) | 7 | |
| 8-36 | AHVEGIGWQGAVCDGAVAGTTGQSRRMEA (SEQ ID NO: 17) | 29 | SHA domain 1 |
| 37-50 | AVIATSGTGGVCAN (SEQ ID NO: 18) | 14 | |
| 51-83 | AHLADIGWQGWACAADGKAVTVGTTGQSRRMEA (SEQ ID NO: 19) | 33 | SHA domain 2 |
| 84-96 | LGLQVGNGSVAAQ (SEQ ID NO: 20) | 13 | |
| 97-126 | AHVADYGWLNAEGGNPVYVGTTGQSRRMEA (SEQ ID NO: 21) | 30 | SHA domain 3 |
| 127-131 | VRIWV (SEQ ID NO: 22) | 5 | |

Table 3 demonstrates the homology between ChW and SHA domains. SHA domains 1, 2, and 3 were compared to *Clostridium acetobutylicum* ATCC 824 protein Q97E41, which was found using SMART (simple modular architecture research tool). The key signature of ChW domains, tryptophan (W), is underlined.

TABLE 3

| | | |
|---|---|---|
| ChW domain | AHVQNIGWQDWVSNGAEAGTDGKGLRVEALRIKLENMP (SEQ ID NO: 23) | Identity |

TABLE 3-continued

| | | |
|---|---|---|
| SHA domain 1 | AHVEGIGWQGAVCDGAVAGTTGQSRRMEA (SEQ ID NO: 17) | 17/29 = 59% |
| SHA domain 2 | AHLADIGWQGWACAADGKAVTVGTTGQSRRMEA (SEQ ID NO: 19) | 13/33 = 39% |
| SHA domain 3 | AHVADYGWLNAEGGNPVYVGTTGQSRRMEA (SEQ ID NO: 21) | 11/30 = 37% |

Example 6: Characterization of the Carbohydrate-Binding Properties of SHA

Figure 6A:
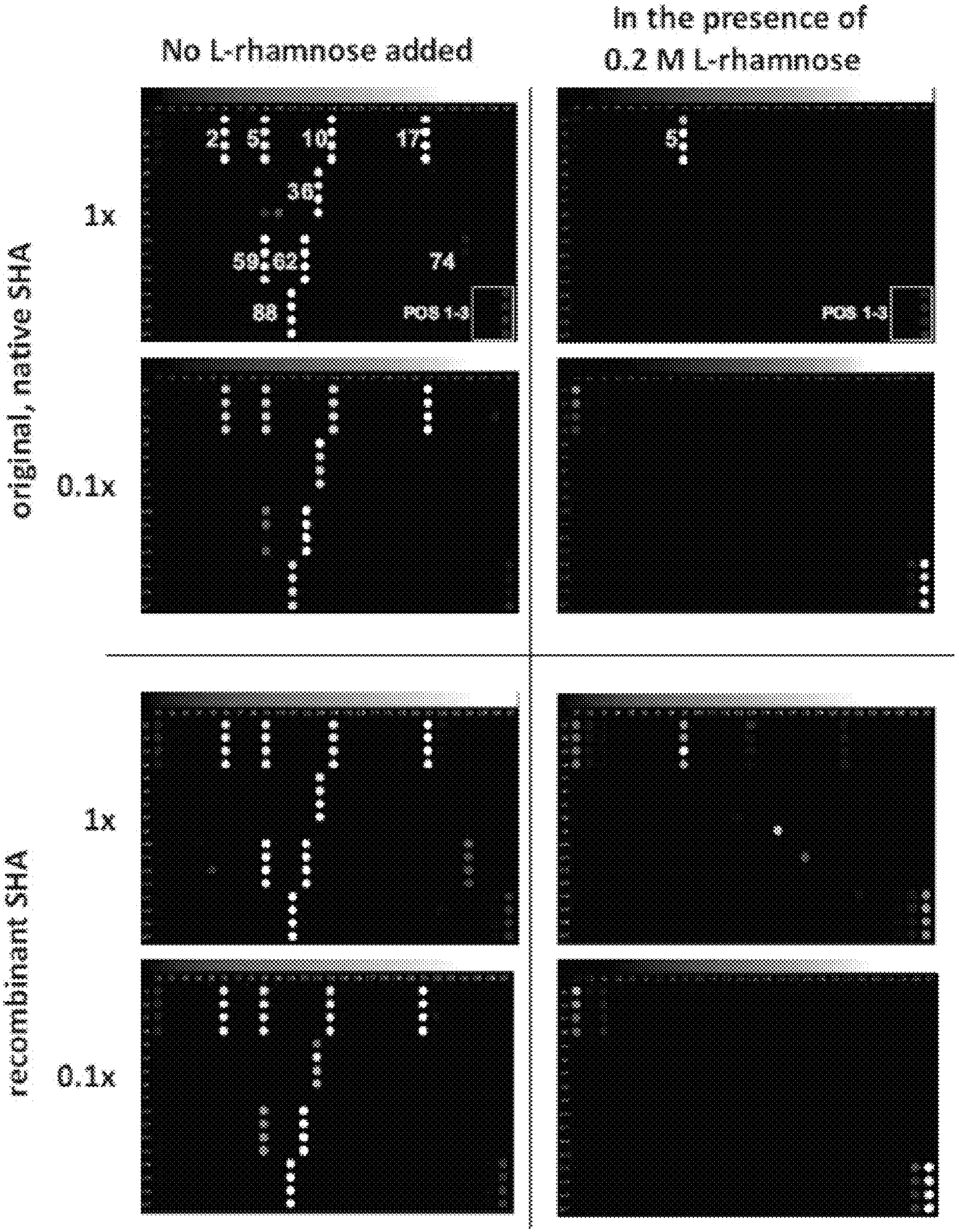
FIGS. 6A-6C show glycan microarray analysis of archived and recombinant SHA.
Figure 6B:
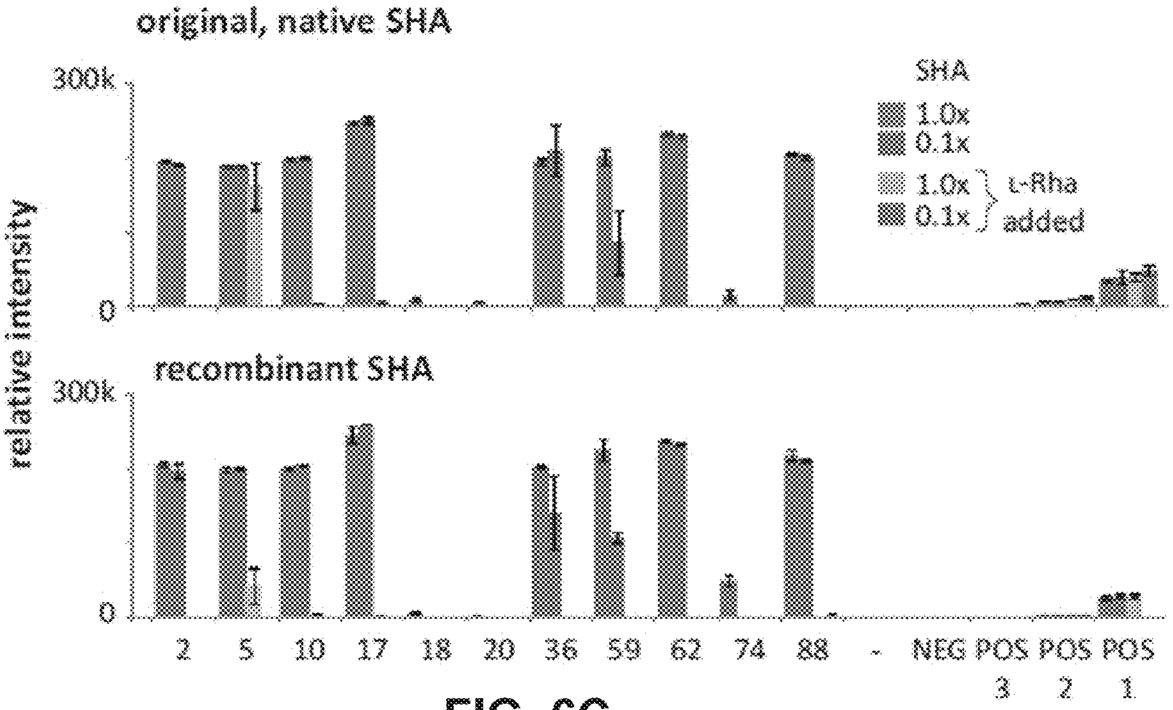
Figure 6C:
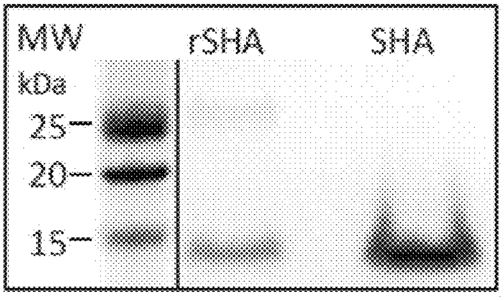
Figure 7:
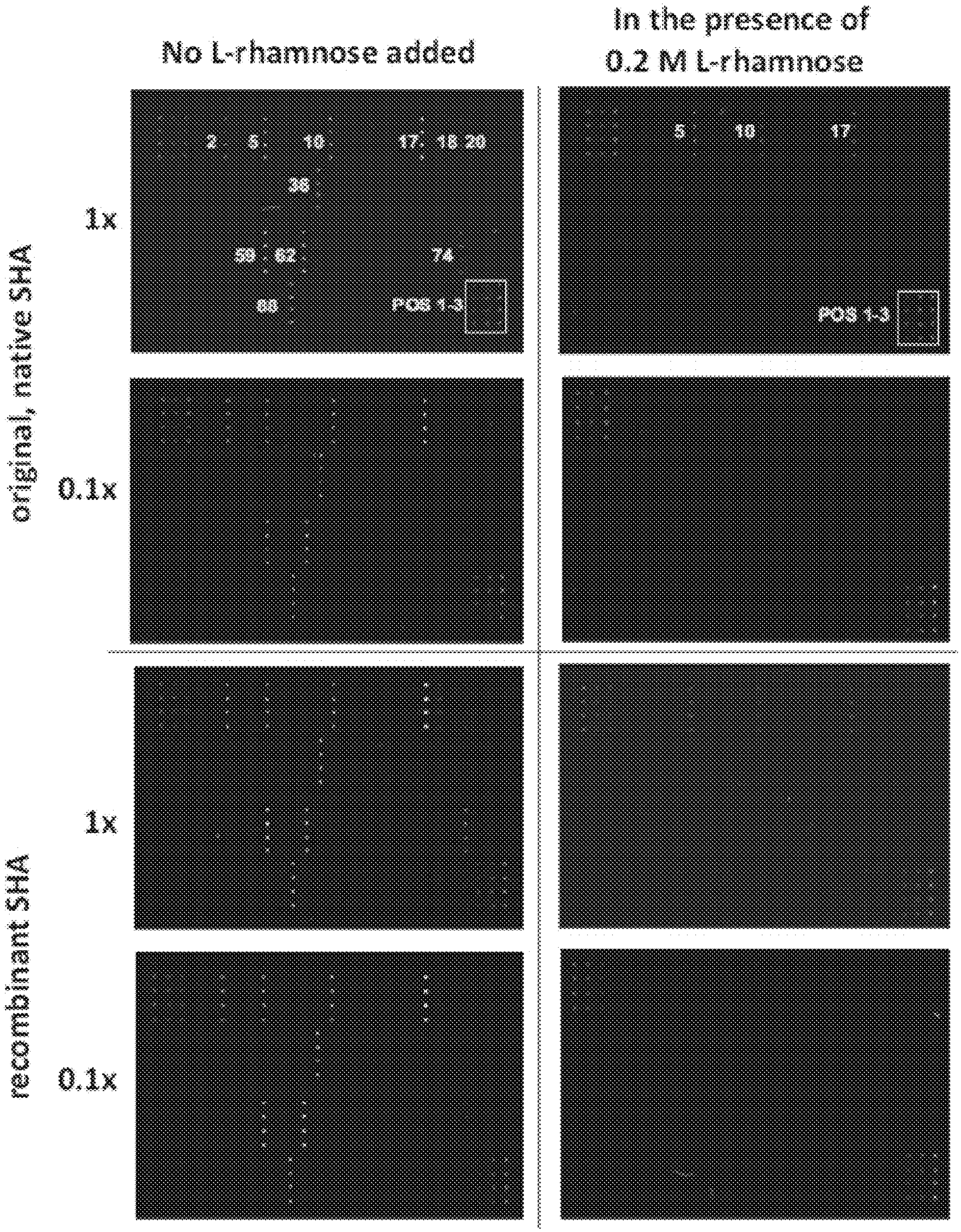
FIG. 7 shows glycan microarray, original readouts from fluorescence scanner. Raw data of glycan-specific fluorescent signals in the absence (left panel) or presence of 0.2 M L-rhamnose (right panel) using two different concentrations (1×, 0.1×) of SHA (top) or rSHA (bottom). Yellow numbers indicate array positions with positive signals (see FIG. 6B for glycan identity).

In contrast to archived SHA, the first Trx-SHA fusion protein generated as described above was poorly soluble and not suitable for functional analyses. Therefore, a novel construct that encoded an *E. coli* codon-optimized, His-tagged, Trx-SMT3 (SUMO family protein)-SHA(A108E) fusion protein was expressed. This protein was refolded on the nickel NTA column in the presence of D-galactose, and soluble recombinant SHA (rSHA) was cleaved off from the Trx-SMT3 portion using His-tagged Ulp1 (8). The purified rSHA is shown in FIG. 6C, together with archived SHA. To determine the carbohydrate-binding specificity of SHA and rSHA, the commercially available Glycan Array 100 slides were used, on which 100 synthetic glycans of the most frequently identified structures in the literature are mounted in each of four sub-arrays. The glycan binding was measured using two distinct concentrations of biotin-labeled SHAs (1×: 20 μg/ml and 0.1×: 2 μg/ml) in the absence and presence of 0.2 M L-rhamnose as a competitive inhibitor. Both SHA and rSHA showed identical carbohydrate-binding specificities (FIGS. 6A, 6B, and 7). Strong signals were observed for SHA/rSHA binding to: β-Gal-; α-Rha-; Gal-α-1,3-Gal-β-1,3-GlcNAc-β-; Gal-α-1,3-Gal-β-1,4-Glc-β-; Gal-α-1,4-Gal-β-1,3-GlcNAc-β-; Gal-α-1,3-(Fuc-α-1,2)-Gal-β-[Blood B antigen trisaccharide]; Gal-α-1,3-(Fuc-α-1,2)-Gal-β-1,4-Glc-β- [Blood B antigen tetrasaccharide]; and Gal-α-1,3-Gal-β-. Also, weaker, but still significant, binding to Gal-α-1,4-Gal-β-1,4-Glc-β-; GalNAc-β-1,3-Gal-β-1,4-Glc-β-; and Gal-α-1,4-Gal-β-1,4-GlcNAc-β- was observed. SHA/rSHA did not bind to the remaining 89 chip-immobilized glycans (Table 4).

TABLE 4

| Array Position | Glycan |
|---|---|
| 1 | β-Glc-Sp |
| 3 | α-Man-Sp |
| 4 | α-Fuc-Sp |
| 6 | β-GlcNAc-Sp |
| 7 | β-GalNAc-Sp |
| 8 | Tobramycin |
| 9 | Gal-β-1,3-GlcNAc-β-Sp |
| 11 | Neu5Ac-α-2,3-Gal-β-1,3-GlcNAc-β-Sp |
| 12 | Neu5Ac-α-2,6-Gal-β-1,3-GlcNAc-β-Sp |
| 13 | Neu5Gc-α-2,3-Gal-β-1,3-GlcNAc-β-Sp |
| 14 | Neu5Gc-α-2,6-Gal-β-1,3-GlcNAc-β-Sp |
| 15 | Gal-β-1,3-(Fuc-α-1,4)-GlcNAc-β-[Lewis A]-Sp |
| 16 | Gal-β-1,4-Glc-β-Sp |
| 19 | GlcNAc-β-1,3-Gal-β-1,4-Glc-β-Sp |
| 21 | Neu5Ac-α-2,3-Gal-β-1,4-Glc-β-Sp |
| 22 | Neu5Ac-α-2,6-Gal-β-1,4-Glc-β-Sp |
| 23 | Neu5Gc-α-2,3-Gal-β-1,4-Glc-β-Sp |
| 24 | Neu5Ac-α-2,6-Gal-β-1,4-Glc-β-Sp |
| 25 | Gal-β-1,4-(Fuc-α-1,3)-Glc-β-Sp |
| 26 | GalNAc-β-1,3-Gal-α-1,4-Gal-β-1,4-Glc-β-Sp |

TABLE 4-continued

| Array Position | Glycan |
|---|---|
| 27 | GlcNAc-β-1,6-GlcNAc-β-Sp |
| 28 | 4-P-GlcNAc-b-1,4-Man-b-Sp |
| 29 | Glc-α-1,2-Gal-α-1,3-Glc-α-Sp |
| 30 | Gal-β-1,3-GalNAc-α-Sp |
| 31 | Gal-β-1,4-GlcNAc-β-Sp |
| 32 | Gal-β-1,4-(Fuc-α-1,3)-GlcNAc-β-[Lewis X]-Sp |
| 33 | Neu5Ac-α-2,3-Gal-β-1,4-(Fuc-α-1,3)-GlcNAc-β-[Sialyl Lewis X]-Sp |
| 34 | Neu5Ac-α-2,3-Gal-β-1,3-(Fuc-α-1,4)-GlcNAc-β-[Sialyl Lewis A]-Sp |
| 35 | Neu5Gc-α-2,3-Gal-β-1,3-(Fuc-α-1,4)-GlcNAc-β-[Sialyl Lewis A]-Sp |
| 37 | Gal-β-1,4-GlcNAc-β-1,3-Gal-β-1,4-Glc-β-[LNnT]-Sp |
| 38 | GlcA-β-1,4-GlcNAc-α-1,4-GlcA-β-Sp |
| 39 | GlcNAc-β-1,6-(Gal-β-1,3)-GalNAc-α-O-Ser-Sp4 |
| 40 | Neu5Ac-α-2,3Gal-β-1,4-(6S)GlcNAc-β-Sp |
| 41 | GalNAc-β-1,4-GlcNAc-β-Sp2 |
| 42 | Neu5Ac-α-2,8-Neu5Ac-α-2,3-Gal β-1,4-Glc-β-Sp |
| 43 | Neu5Gc-α-2,8-Neu5Ac-α-2,3-Gal-β-1,4-Glc-β-Sp |
| 44 | GalNAc-α-1,3-(Fuc-α-1,2)-Gal-β-1,4-Glc-β-[Blood A antigen tetrose]-Sp1 |
| 45 | GlcNAc-β-1,2-Man-α-Sp |
| 46 | Neu5Ac-α-2,3-Gal-β-Sp1 |
| 47 | Gal-β-1,3-GalNAc-β-1,3-Gal-β-Sp1 |
| 48 | Glc-α-1,2-Gal-α-Sp |
| 49 | Gal-β-1,4-(Fuc-α-1,3)-GlcNAc-β-1,3-Gal-β-Sp1 |
| 50 | Neu5Ac-α-2,3-Gal-β-1,4-(Fuc-α-1,3)-Glc-β-[3-Sialyl-3-fucosyllactose/F-SL]-Sp1 |
| 51 | GlcNAc-β-1,4-GlcNAc-β-Sp1 |
| 52 | β-D-GlcA-Sp |
| 53 | Gal-β-1,4-(6S)GlcNAc-β-Sp |
| 54 | GlcNAc-α-1,3-(Glc-α-1,2-Glc-α-1,2)-Gal-α-1,3-Glc-α-Sp |
| 55 | Gal-β-1,3-GalNAc-β-1,4-(Neu5Gc-α-2,3)-Gal-β-1,4-Glc-β-Sp1 |
| 56 | Sisomicin Sulfate |
| 57 | GalNAc-α-1,3-(Fuc-α-1,2)-Gal-β-[Blood A antigen trisaccharide]-Sp1 |
| 58 | Fuc-α-1,2-Gal-β-1,4-GlcNAc-β-[Blood H antigen trisaccharide]-Sp1 |
| 60 | Fuc-α-1,2-Gal-β-1,3-GlcNAc-β-1,3-Gal-β-1,4-Glc-β-[LNFP I]-Sp1 |
| 61 | Fuc-α-1,2-Gal-β-1,4-Glc-β-[Blood H antigen trisaccharide]-Sp1 |
| 63 | (Fuc-α-1,2)-Gal-β-1,4-(Fuc-α-1,3)-GlcNAc-β-[Lewis Y]-Sp1 |
| 64 | (Fuc-α-1,2)-Gal-β-1,3-(Fuc-α-1,4)-GlcNAc-β-[Lewis B]-Sp1 |
| 65 | Gal-β-1,3-(Fuc-α-1,4)-GlcNAc-β-1,3-Gal-β-1,4-(Fuc-α-1,4)-Glc-β-[Lewis A]-Sp1 |
| 66 | Gal-β-1,3-GalNAc-β-Sp1 |
| 67 | Gal-β-1,3-(Neu5Ac-α-2,6)-GalNAc-β-Sp |
| 68 | Neu5Ac-α-2,6-Gal-β-1,3-GalNAc-β-Sp |
| 69 | Neu5Ac-α-2,6-Gal-β-1,3-(Neu5Ac-α-2,6)-GalNAc-β-Sp |
| 70 | Neu5Ac-α-2,3-Gal-β-1,3-(Neu5Ac-α-2,6)-GalNAc-β-Sp |
| 71 | Neu5Ac-α-2,6-(Neu5Ac-α-2,3)-Gal-β-1,3-GalNAc-β-Sp |
| 72 | GalNAc-β-1,4-(Neu5Ac-α-2,3)-Gal-β-1,4-Glc-β-[GM2]-Sp |
| 73 | GalNAc-β-1,4-(Neu5Ac-α-2,8-Neu5Ac-α-2,3)-Gal-β-1,4-Glc-β-[GD2]-Sp |
| 75 | β-D-Rha-Sp |
| 76 | Glc-α-1,4-Glc-β-Sp1 |
| 77 | Glc-α-1,6-Glc-α-1,4-Glc-β-Sp1 |
| 78 | Maltotriose-β-Sp1 |
| 79 | Glc-α-1,6-Glc-α-1,6-Glc-β-Sp1 |
| 80 | Maltotetraose-β-Sp1 |
| 81 | GlcNAc-α-1,4-GlcA-β-1,4-GlcNAc-α1,4-GlcA-β-Sp |
| 82 | Maltohexaose-β-Sp1 |
| 83 | Maltoheptaose-β-Sp1 |
| 84 | Acarbose-β-Sp1 |
| 85 | D-pentamannuronic acid-β-Sp1 |
| 86 | L-pentaguluronic acid-β-Sp1 |
| 87 | D-cellose-β-Sp1 |
| 89 | β-1,4-Xylotetrose-Sp1 |
| 90 | Chitin-trisaccharide-Sp1 |
| 91 | KDN-α-2,8-Neu5Ac-α-2,3-Gal-β-1,4-Glc-β-Sp |
| 92 | Neu5Ac-α-2,8-Neu5Gc-α-2,3-Gal-β-1,4-Glc-β-Sp |
| 93 | Neu5Ac-α-2,8-Neu5Ac-α-2,8-Neu5Ac-α-2,3-Gal-β-1,4-Glc-β-Sp3 |
| 94 | Neu5Ac-a-2,8-Neu5Ac-α-2,6-Gal-b-1,4-Glc-Sp5 |
| 95 | Gal-β-1,3-GalNAc-β-1,4-(Neu5Ac-α-2,3)-Gal-β-1,4-Glc-β-Sp1 |
| 96 | Gentamicin Sulfate |

TABLE 4-continued

| Array Position | Glycan |
|---|---|
| 97 | Kanamycin sulfate |
| 98 | Geneticin Disulfate Salt (G418) |
| 99 | Neomycin trisulfate |
| 100 | SGP |

Linkers:
Sp: $OCH_2CH_2CH_2NH_2$
Sp1: $NH(CH_3)OCH_2CH_2NH_2$
Sp2: $OCH_2CH_2NH_2$
Sp3: $O(CH_2)_3NHCOCH_2(OCH_2CH_2)_5CH_2CH_2NH_2$
Sp4: $OCH_2CH(COOH)NH_2$
Sp5: $NH_2$(-o-phenyl)-CONH-$CH_2CH_2NH_2$ In the presence of L-rhamnose, SHA/rSHA binding to all glycans, except α-Rha, was competitively inhibited (FIGS. 6A and 6B). These results are consistent with earlier hemagglutination inhibition or equilibrium dialysis observations in which SHA bound to L-rhamnose with a higher affinity than to D-galactose (2-4).

Example 7: Sequence Comparison of SHA and Putative Homologues

Figure 8A:
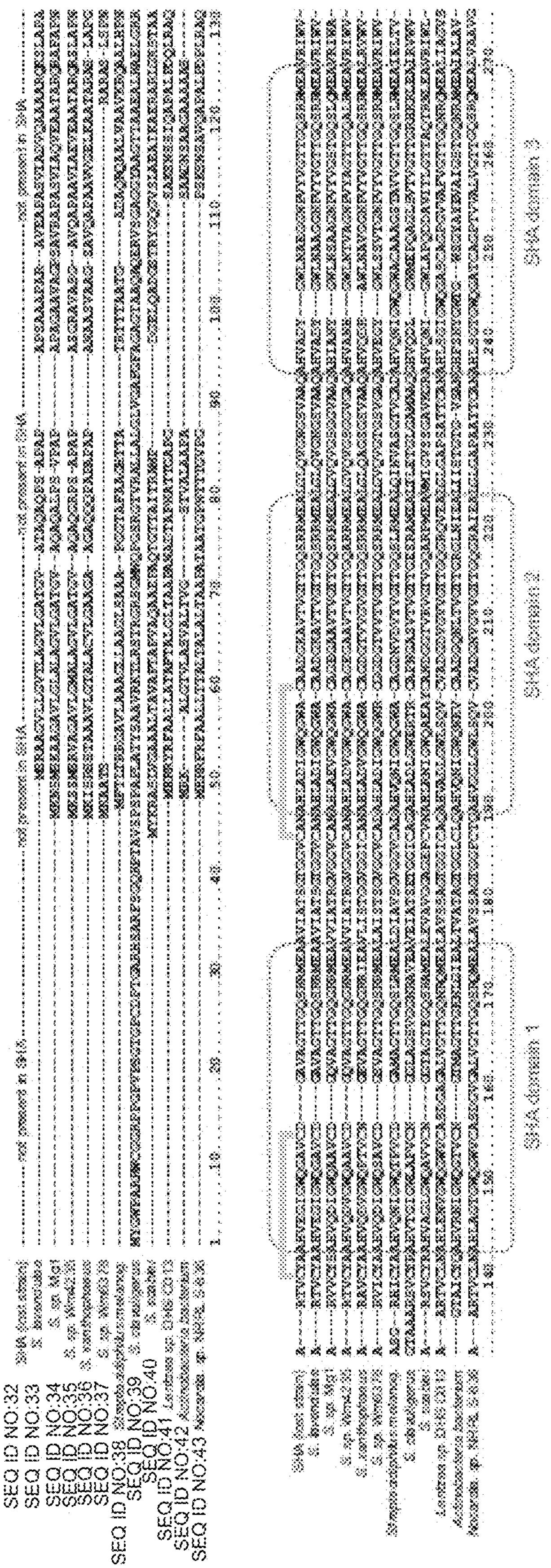
FIGS. 8A-8C show SHA and homologues.

SHA homologues were identified not only in the *Streptomyces* genome, but also in the genomes of other microorganisms. Eleven putative SHA homologues with more than 50% homology to the SHA sequence were identified as N-terminally truncated hypothetical proteins in the genomes of *S. lavendulae*, S. sp. Mg1, S. sp. Wm4235, *S. xanthophaeus*, S. sp. Wm6378, *S. clavuligerus, S. scabiei, Streptacidiphilus melanogenes, Lentzea* sp. DHS C013, Actinobacteria bacterium, and *Nocardia* sp. NRRL S-836 (FIG. 8A). The N-terminal sequence of the putative SHA homologues varied among homologues, and a corresponding sequence was absent in SHA. In contrast, the C-terminal domain was conserved between SHA and its homologues. Compared to the 131 amino acids of the SHA sequence, the SHA homologues contained 15-133 additional amino acids at the N-terminal end, for a total of 172-265 amino acids.

Figures 8B, 8C:
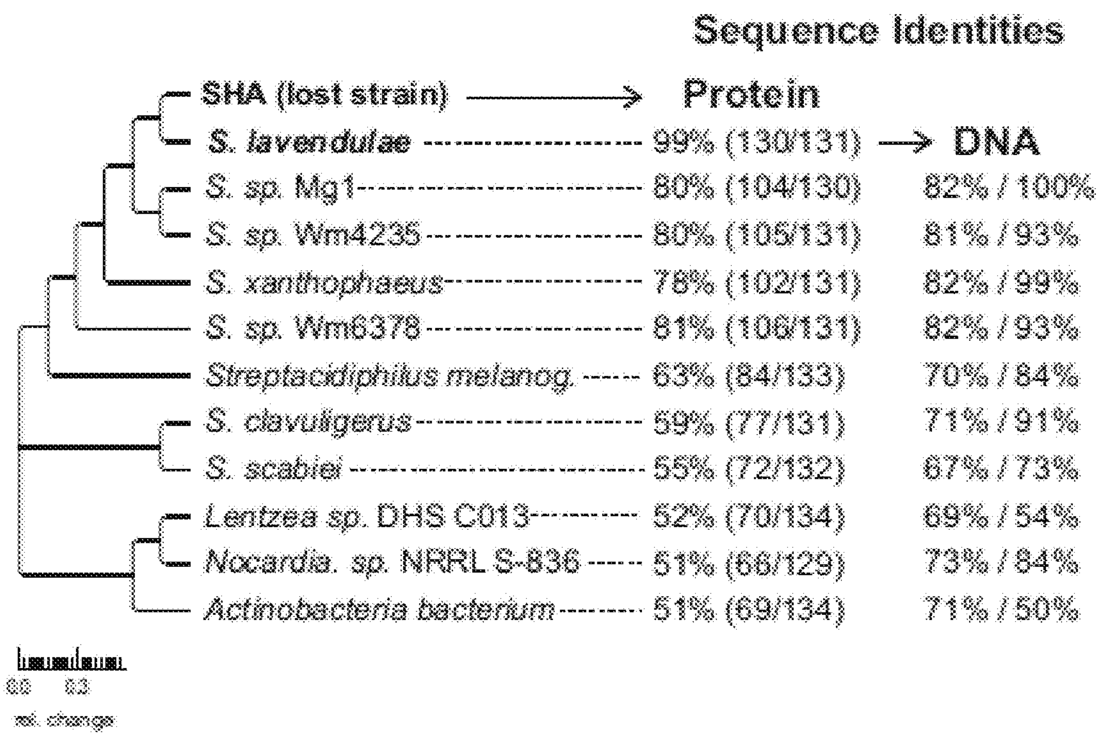

To compare protein and DNA sequences of SHA and its homologues, a phylogenetic tree was generated (FIG. 8B). Protein sequence homology ranged from 51-99%. In the absence of SHA genetic information, *S. lavendulae* DNA (438 bases) was used as the reference query for SHA homologues. DNA sequence homology ranged from 67-82%.

The primary sequence of SHA is principally made up of three homologous “SHA domains,” each consisting of 29 to 33 amino acids (Table 2). Sequence identity between the three SHA domains ranged from 60% to 70% (FIG. 8C). The three SHA domains contained an identical stretch of eleven consecutive amino acids, GTTGQSRRMEA (SEQ ID NO: 24), at the C-terminus. Together, they comprised 92 amino acids, 70% of the total 131 amino acids in SHA. Furthermore, the SHA domains showed homology to tryptophan-rich ChW domains. ChW domains are almost exclusively found in the *Clostridium acetobutylicum* species (9,10). Protein Q97E41 of *Clostridium acetobutylicum* ATCC 824 was identified as the closest clostridial homologue to SHA, using SMART (simple modular architecture research tool). It had 59%, 39%, and 37% identity for SHA domains 1, 2, and 3, respectively (Table 3).

Example 8: NMR Identification of Tryptophan Residues

Figure 9:
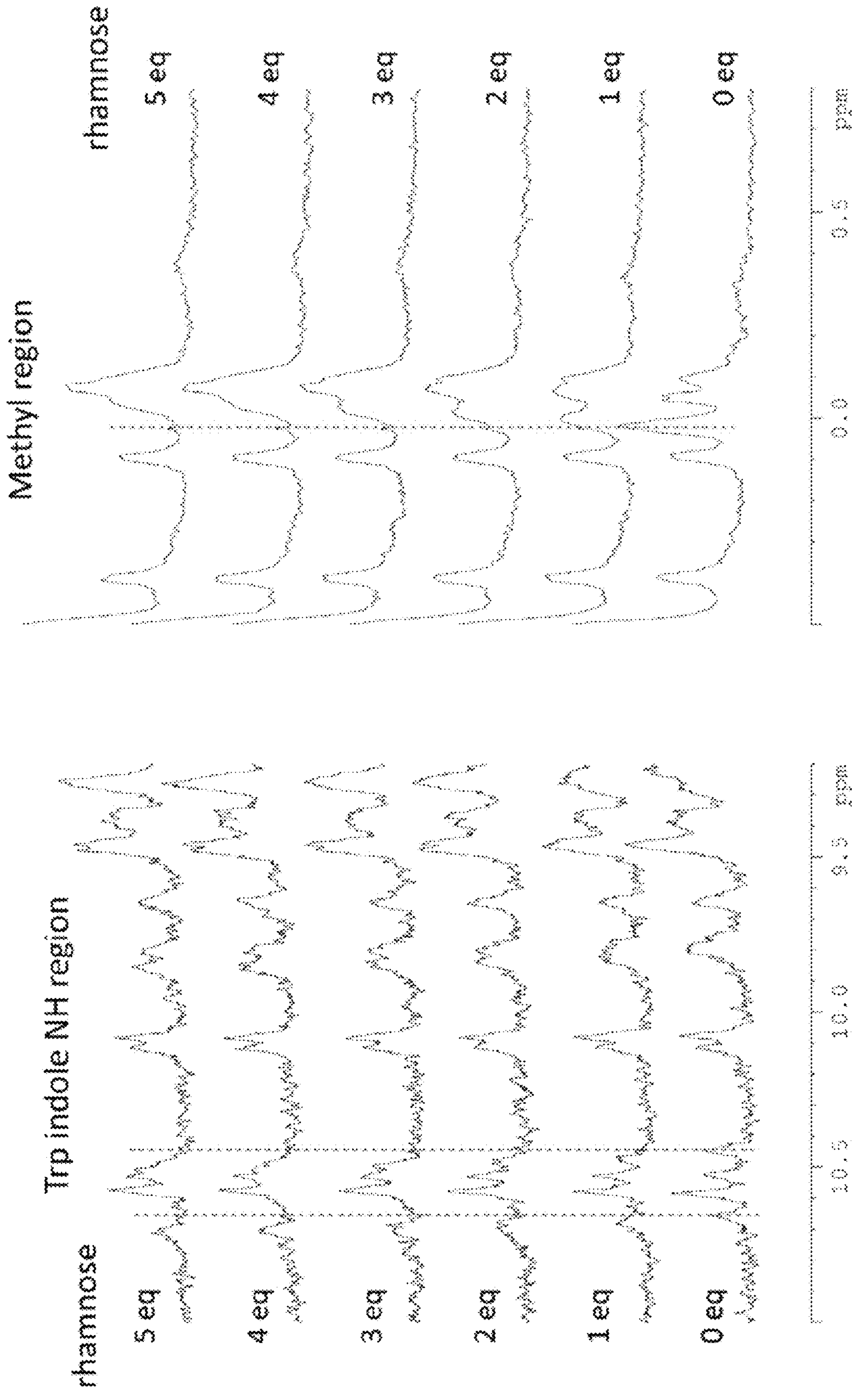
FIG. 9 shows $^{1}$H-NMR analysis for L-rhamnose binding to archived SHA. L-rhamnose was added to the SHA solution from 1 to 5 equivalents. The indole NH region (left) and methyl region (right) of 1D $^{1}$H-NMR spectra are shown. Dashed red lines are included for alignment. Chemical shift changes observed for specific peaks indicate binding of L-rhamnose to SHA.

NMR titration was used to show that the addition of L-rhamnose caused chemical shifts in NMR signals from SHA in the tryptophan indole NH and methyl group regions (FIG. 9). This indicates that the ChW tryptophan residues are most likely directly involved in carbohydrate binding.

Example 9: Demonstration of rSHA Binding to Microbial Surfaces

Figure 10:
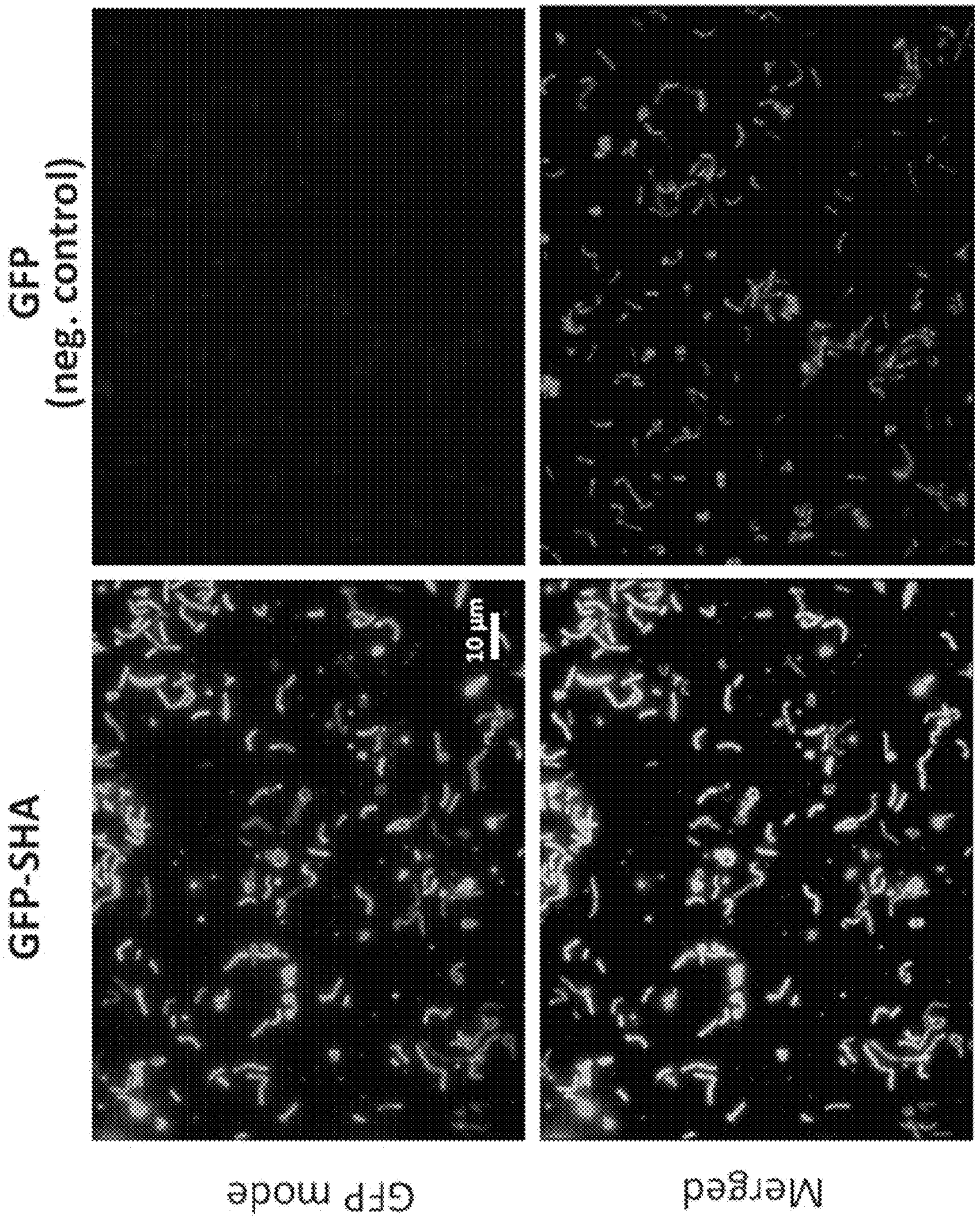
FIG. 10 shows representative fluorescent micrographs of *Lactobacillus casei* (Shirota) cells stained with recombinant GFP-SHA fusion protein (top left panel). Recombinant GFP was used as a negative control (top right panel). DAPI counterstaining is shown in blue in the merged micrographs (bottom).

Due to the loss of the original SHA-producing *Streptomyces* strain 27S5, the biological role of SHA is difficult to characterize. SHA binding to microbial cell surfaces was demonstrated in this example. A green fluorescent protein (GFP) SHA fusion protein (GFP-SHA) was constructed and used to stain various bacteria and fungi, and performed fluorescence microscopy. A representative example is shown in FIG. 10, which demonstrates the binding of GFP-SHA to *Lactobacillus casei* Shirota cells. *L. casei* Shirota is rich in L-rhamnose-containing cell wall glycans (11). The binding of SHA to microbial glycans may imply a role for SHA in complex microbial communication.

Example 10: $^{68}$Ga PET Imaging of CD-1 Mice

Figure 11:
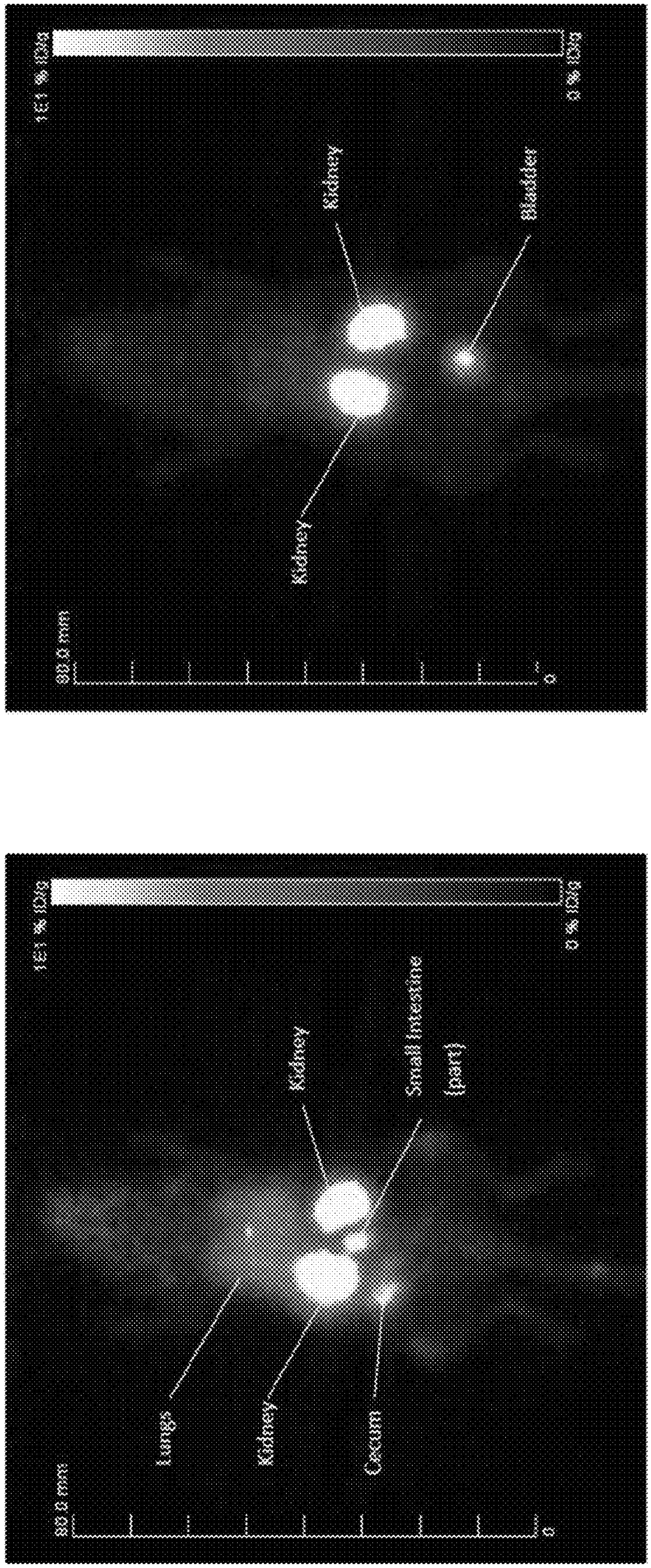
FIG. 11 demonstrates $^{68}$Ga PET imaging of CD-1 mice. These are the areas that contain microorganisms. While the control mouse only shows radioactivity uptake in the kidneys and in the bladder, which is typical for small proteins, the $^{68}$Ga-DOTA-GFP-SHA-injected mouse reveals additional strong signals from the cecum and the small intestine. The latter are known internal organs that naturally contain a rhamnose-rich microbial flora.
Figure 12:
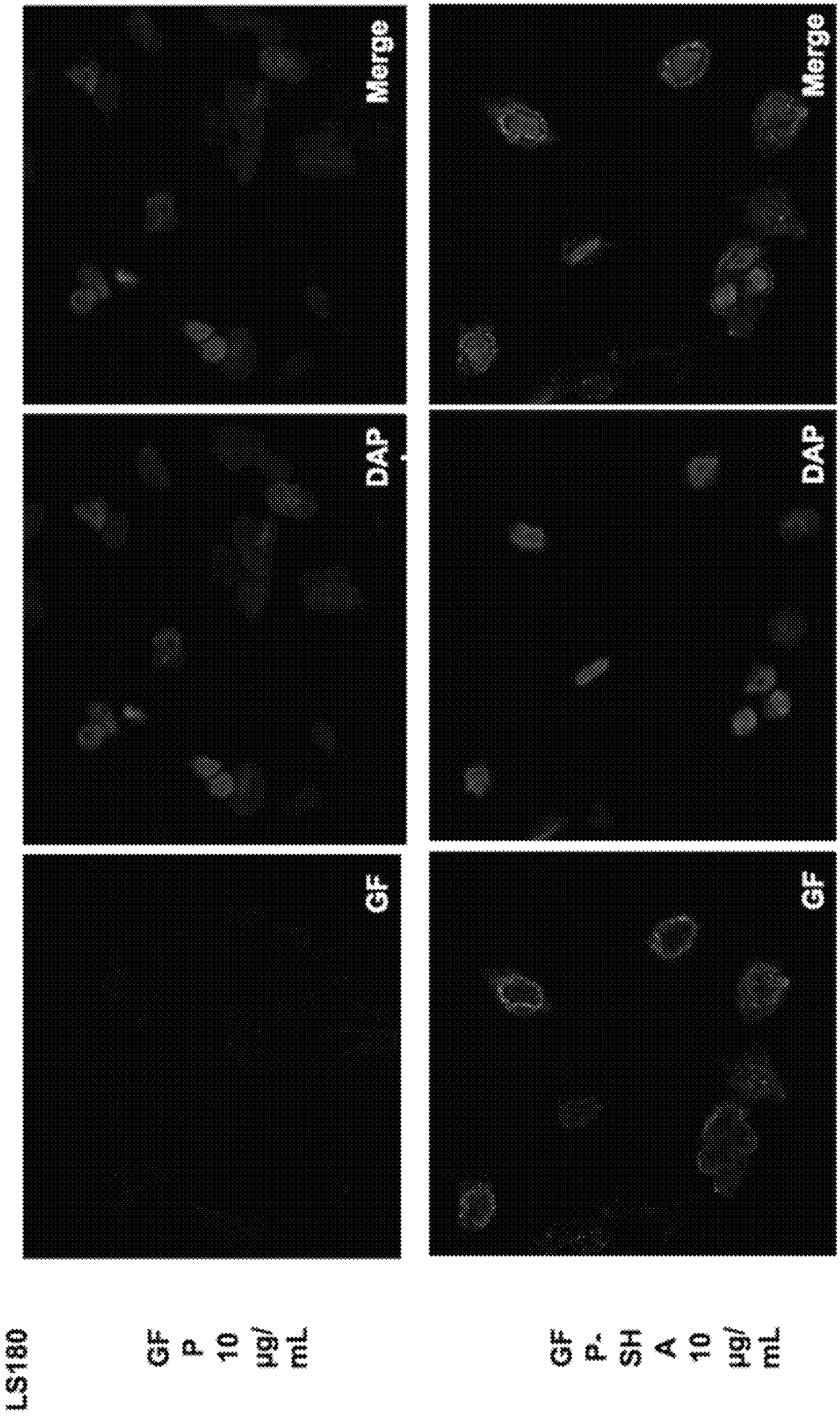
FIG. 12 shows GFP-SHA staining of LS180 cell surfaces. Cells were stained with either 10 μg/mL GFP-SHA or a GFP-only control as indicated, followed by visualization using a Zeiss LSM 880 confocal microscope. DAPI was used as a counterstain to label nuclear DNA. GF=GFP mode; DAP=DAPI mode; Merge=GF+DP overlay.

PET imaging was performed using with 68-gallium labeled GFP-SHA fusion protein in mice. $^{68}$Ga was obtained from a $^{68}$Ge/$^{68}$Ga generator system and chelated with 1,4,7,10-tetraazacyclododecane-1,4,7,10-tetraacetic acid (DOTA)-labeled GFP-SHA. 5.1 MBq of the resulting $^{68}$Ga-GFP-SHA was injected through the tail vein of female CD1 mice, and PET imaging was conducted at the City of Hope Small Animal Imaging Core facility. As a control $^{68}$Ga-DOTA-scFv was used. The PET scanning was conducted 1.5 hours after intravenous injection of the PET imaging agent. The $^{68}$Ga-DOTA-scFv had no specificity for rhamnose-containing microorganisms. As shown in FIG. 11, $^{68}$Ga-labeled GFP-SHA specifically labels parts of the small intestine and the cecum. These are the areas that contain microorganisms.

While the control mouse only shows radioactivity uptake in the kidneys and in the bladder, which is typical for small proteins, the $^{68}$Ga-DOTA-GFP-SHA-injected mouse reveals additional strong signals from the cecum and the small intestine. The latter are known internal organs that naturally contain a rhamnose-rich microbial flora.

Example 11: Staining of LS180 Cells with GFP-SHA

LS180 human colon adenocarcinoma cells were grown in Dulbecco’s Modified Eagle’s Medium (DMEM) with 4.5 g/L glucose, L-glutamine, and sodium pyruvate (Corning) with seeding at 60,000 cells/well in a 24-well dish containing glass coverslips. Cells were adhered overnight, after which media was removed and coverslips washed 3× with phosphate-buffered saline (PBS). Paraformaldehyde (4%) was then added with incubation for 15 min at 25° C., followed by washing 3× with PBS and blocking with 5% bovine serum albumin (BSA) in PBS for one hour. Cells were then incubated with 10 μg/mL GFP-SHA or a GFP-only control diluted in 5% BSA in PBS overnight at 4° C. Following staining, cells were washed 3× with PBS and then mounted on glass slides with 10 μL Fluoroshield mounting medium with 4',6-diamidino-2-phenylindole (DAPI, Abcam). Cells were then visualized using a Zeiss LSM 880 with Airyscan confocal microscope, employing excitation at 488 nm for green fluorescence and 358 nm for DAPI staining. As shown in FIG. 11, GFP-SHA binds to the surface of LS180 cells, while GFP alone does not.

Example 12: SHA Imaging of Cancer Tissues Using FITC-Labeled SHA

SHA was labeled with FITC using amine coupling chemistry. Briefly, 100 μL of SHA in 0.1 M sodium carbonate, pH 9.0 at 2 mg/mL concentration was incubated for 1 hour with 50 μg/mL of FITC in DMSO on rotary shaker at 22° C. (protected from light). After incubation, the reaction was quenched by adding 20 μL of 1 M ethanolamine following 30 minutes incubation at 22° C. Purification of labeled protein was performed using 5 kDa MW cut off filter. The degree of labeling at 1.7 (Fluorophore/Protein) was calculated using 68,000 $cm^{-1}M^{-1}$ molar extinction coefficient of the dye at pH 8.0 at 494 nm.

7 μm thick consecutive sections from each block of a paraffinized formalin fixed tissue sample were cut and baked, and each section was placed on a separate slide. Sections were deparaffinized using sequential immersions into 2 xylene baths (10 minutes each), dehydrated with 4 baths of decreasing alcohol concentrations (100%, 95%, 70%, and 50%, 5 minutes each) and 2 baths with deionized $H_2O$. Slides then were rehydrated with 1×PBS for 10 minutes following heat-induced antigen unmasking procedure. Briefly, slides for 8 minutes at 95° C. in 10 mM citrate buffer, pH 6.0, rinsed gently with deionized $H_2O$ and then with 1×PBS. Staining procedure began with blocking of slides overnight at 4° C. with 1×PBS with 5% bovine serum albumin following incubation with FITC-SHA at 20 μg/mL for 1 hour at 22° C. in blocking buffer. Slides were washed three times with 1×PBS. Counterstaining was performed with 4',6-diamidino-2-phenylindole (DAPI, 3 μM for 10 minutes, washed with 1×PBS three times and examined using a fluorescent microscope. Hematoxylin and Eosin (H&E) staining was performed using standard hematoxylin and eosin staining procedure (www.nationaldiagnostics-.com). Microscopy was performed with Zeiss Axio Observer II Inverted Fluorescence Microscope (Jena, Germany) and ZEN2 (Blue Edition) software.

Figure 13:
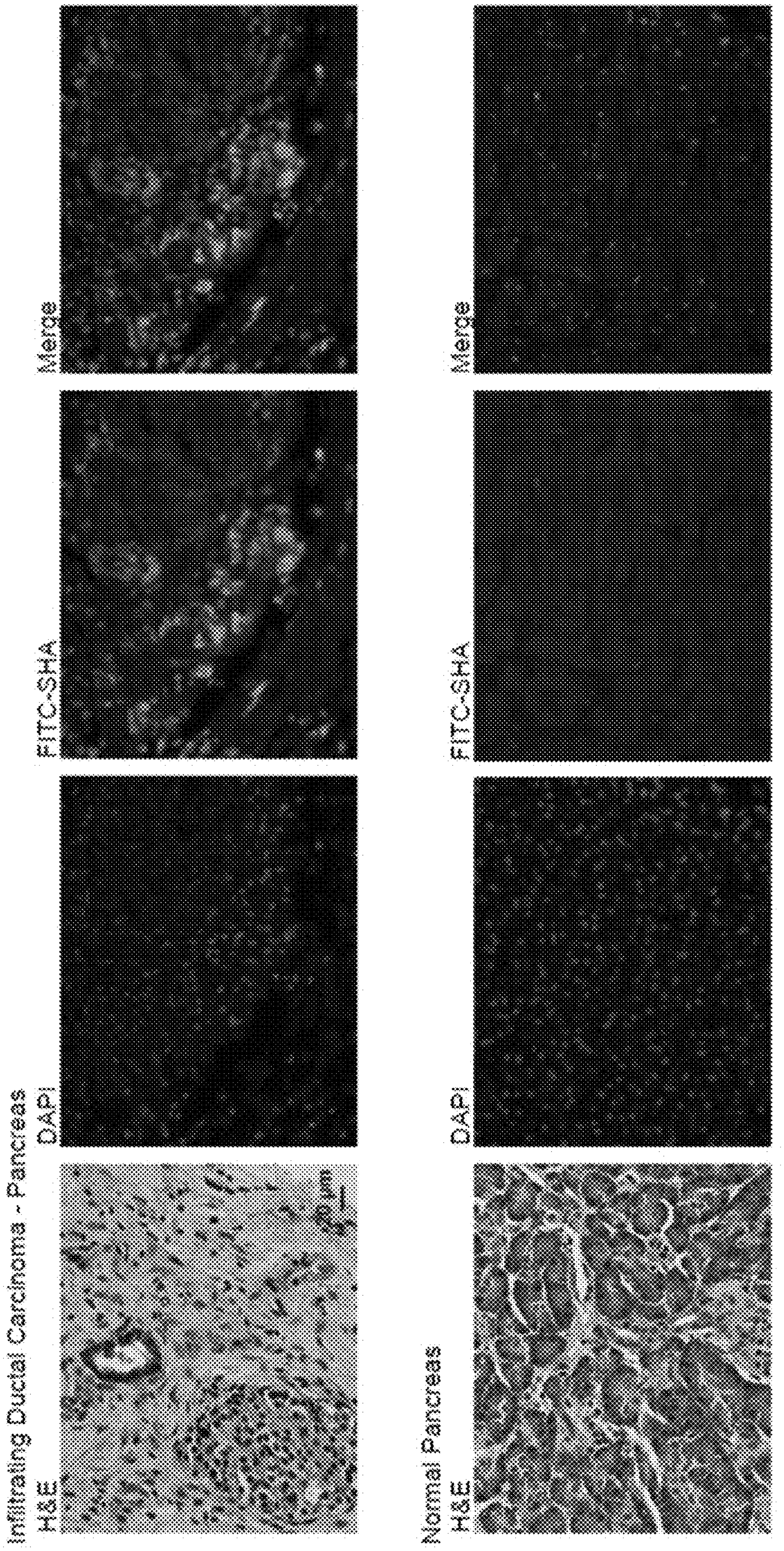
FIG. 13 shows hematoxylin and eosin (H&E) and fluorescent staining of consecutive slices of cancerous and normal tissues from City of Hope patient. 40× magnification.

The FITC-SHA-stained tissues of the infiltrating ductal carcinoma case (which was an infiltrating, malignant and abnormal proliferation of neoplastic cells in the breast tissues advanced to the tumor in the pancreas) were examined. As shown in FIG. 13, the SHA clearly labeled cells in tumor tissues. Pancreatic ductal carcinoma gave very strong staining. Other tumors did too (data not shown). The precise target that was SHA-labeled in the tumor sections is unknown at this point, but not wishing to be bound by any theory, it might be due to abnormal mucins secreted by tumor cells.

Significant difference in fluorescent signal was observed between the two groups, the pancreatic cancer tissue and the normal tissue stained with FITC-SHA protein demonstrating that the FITC-SHA has higher affinity to cancerous cells than to the normal cells.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Fujita, Y., Oishi, K., and Aida, K. (1972) Hemagglutination by culture broth of Actinomycetes and *Aspergillus. J. Gen. Appl. Microbiol.* 18, 73-75
2. Fujita, Y., Oishi, K., and Aida, K. (1973) Sugar specificity of anti-B hemagglutinin produced by *Streptomyces* sp. *Biochemical and biophysical research communications* 53, 495-501
3. Fujita, Y., Oishi, K., Suzuki, K., and Imahori, K. (1975) Purification and properties of an anti-B hemagglutinin produced by *Streptomyces* sp. *Biochemistry* 14, 4465-4470
4. Fujita-Yamaguchi, Y., Oishi, K., Suzuki, K., and Imahori, K. (1982) Studies on carbohydrate binding to a lectin purified from *Streptomyces* sp. *Biochimica et biophysica acta* 701, 86-92
5. Harrison, J., and Studholme, D. J. (2014) Recently published *Streptomyces* genome sequences. *Microbial biotechnology* 7, 373-380
6. Hoefler, B. C., Konganti, K., and Straight, P. D. (2013) De Novo Assembly of the *Streptomyces* sp. Strain Mg1 Genome Using PacBio Single-Molecule Sequencing. *Genome announcements* 1
7. Fujita, Y. (1976) Studies on hemagglutinins produced by microorganisms. The University of Tokyo
8. Guerrero, F., Ciragan, A., and Iwai, H. (2015) Tandem SUMO fusion vectors for improving soluble protein expression and purification. *Protein expression and purification* 116, 42-49
9. Nolling, J., Breton, G., Omelchenko, M. V., Makarova, K. S., Zeng, Q., Gibson, R., Lee, H. M., Dubois, J., Qiu, D., Hitti, J., Wolf, Y. I., Tatusov, R. L., Sabathe, F., Doucette-Stamm, L., Soucaille, P., Daly, M. J., Bennett, G. N., Koonin, E. V., and Smith, D. R. (2001) Genome sequence and comparative analysis of the solvent-producing bacterium *Clostridium acetobutylicum. Journal of bacteriology* 183, 4823-4838
10. Sullivan, L., Paredes, C. J., Papoutsakis, E. T., and Bennett, G. N. (2007) Analysis of the clostridial hydrophobic with a conserved tryptophan family (ChW) of proteins in *Clostridium acetobutylicum* with emphasis on ChW14 and ChW16/17. *Enzyme and Microbial Technology* 42, 29-43
11. Yasuda, E., Tateno, H., Hirabayashi, J., Iino, T., and Sako, T. (2011) Lectin microarray reveals binding profiles of *Lactobacillus casei* strains in a comprehensive analysis of bacterial cell wall polysaccharides. *Applied and environmental microbiology* 77, 4539-4546
12. Zhang, Q., Ames, J. M., Smith, R. D., Baynes, J. W., and Metz, T. O. (2009) A perspective on the Maillard reaction and the analysis of protein glycation by mass spectrometry: probing the pathogenesis of chronic disease. *Journal of proteome research* 8, 754-769
13. Negre-Salvayre, A., Salvayre, R., Auge, N., Pamplona, R., and Portero-Otin, M. (2009) Hyperglycemia and glycation in diabetic complications. *Antioxidants & redox signaling* 11, 3071-3109
14. Cheng, H. N., and Neiss, T. G. (2012) Solution NMR spectroscopy of food polysaccharides. *Polymer Reviews* 52, 81-114
15. Fujimoto, Z., Jackson, A., Michikawa, M., Maehara, T., Momma, M., Henrissat, B., Gilbert, H. J., and Kaneko, S. (2013) The Structure of a *Streptomyces avermitilis* α-l-

Rhamnosidase Reveals a Novel Carbohydrate-binding Module CBM67 within the Six-domain Arrangement. *The Journal of Biological Chemistry* 288, 12376-12385
16. Lamoth, F. (2016) Galactomannan and 1,3-β-D-Glucan Testing for the Diagnosis of Invasive Aspergillosis. *J. Fungi* 2, 22
17. Tateno, H., Saneyoshi, A., Ogawa, T., Muramoto, K., Kamiya, H., and Saneyoshi, M. (1998) Isolation and characterization of rhamnose-binding lectins from eggs of steelhead trout (*Oncorhynchus mykiss*) homologous to low density lipoprotein receptor superfamily. *The Journal of biological chemistry* 273, 19190-19197
18. Hosono, M., Ishikawa, K., Mineki, R., Murayama, K., Numata, C., Ogawa, Y., Takayanagi, Y., and Nitta, K. (1999) Tandem repeat structure of rhamnose-binding lectin from catfish (*Silurus asotus*) eggs. *Biochimica et biophysica acta* 1472, 668-675
19. Tateno, H., Ogawa, T., Muramoto, K., Kamiya, H., and Saneyoshi, M. (2002) Distribution and molecular evolution of rhamnose-binding lectins in Salmonidae: isolation and characterization of two lectins from white-spotted Charr (Salvelinus leucomaenis) eggs. *Bioscience, biotechnology, and biochemistry* 66, 1356-1365
20. Tateno, H., Ogawa, T., Muramoto, K., Kamiya, H., and Saneyoshi, M. (2002) Rhamnose-binding lectins from steelhead trout (*Oncorhynchus mykiss*) eggs recognize bacterial lipopolysaccharides and lipoteichoic acid. *Bioscience, biotechnology, and biochemistry* 66, 604-612
21. Terada, T., Watanabe, Y., Tateno, H., Naganuma, T., Ogawa, T., Muramoto, K., and Kamiya, H. (2007) Structural characterization of a rhamnose-binding glycoprotein (lectin) from Spanish mackerel (*Scomberomorous niphonius*) eggs. *Biochimica et biophysica acta* 1770, 617-629
22. Tateno, H. (2010) SUEL-related lectins, a lectin family widely distributed throughout organisms. *Bioscience, biotechnology, and biochemistry* 74, 1141-1144
23. Ogawa, T., Watanabe, M., Naganuma, T., and Muramoto, K. (2011) Diversified carbohydrate-binding lectins from marine resources. *Journal of amino acids* 2011, 838914
24. Ozeki, Y., Yokota, Y., Kato, K. H., Titani, K., and Matsui, T. (1995) Developmental expression of D-galactoside-binding lectin in sea urchin (*Anthocidaris crassispina*) eggs. *Experimental cell research* 216, 318-324
25. Watanabe, Y., Tateno, H., Nakamura-Tsuruta, S., Kominami, J., Hirabayashi, J., Nakamura, O., Watanabe, T., Kamiya, H., Naganuma, T., Ogawa, T., Naude, R. J., and Muramoto, K. (2009) The function of rhamnose-binding lectin in innate immunity by restricted binding to Gb3. *Developmental and comparative immunology* 33, 187-197
26. Sharon, N. (1987) Bacterial lectins, cell-cell recognition and infectious disease. *FEBS letters* 217, 145-157
27. Ng, S. K., Huang, Y. T., Lee, Y. C., Low, E. L., Chiu, C. H., Chen, S. L., Mao, L. C., and Chang, M. D. (2014) A recombinant horseshoe crab plasma lectin recognizes specific pathogen-associated molecular patterns of bacteria through rhamnose. *PloS one* 9, el 15296
28. Carpentier, G. (2010) Contribution: Protein Array Analyzer for ImageJ. *ImageJ News* 10, presented at the poster session at the ImageJ User and Developer Conference, Oct. 27-29, 2010
29. Suzanne V. Smith, Marian Jones and Vanessa Holmes (2011). Production and Selection of Metal PET Radioisotopes for Molecular Imaging, Radioisotopes—Applications in Bio-Medical Science, Prof. Nirmal Singh (Ed.), ISBN: 978-953-307-748-2

The invention claimed is:

1. A method of detecting a cancer or tumor in a subject, comprising:

contacting a sample obtained from the subject with a fusion protein comprising a fluorescent protein and a *Streptomyces* hemagglutinin (SHA) protein or a homologue of the SHA protein, wherein the SHA protein has an amino acid sequence represented by SEQ ID NO: 25, the homologue of the SHA protein has an amino acid sequence at least 90%, at least 95%, at least 98%, or at least 99% identical to that of SEQ ID NO: 25, wherein the homologue of the SHA protein comprises SEQ ID NO: 17, SEQ ID NO: 19, and SEQ ID NO: 21; and wherein the fusion protein specifically binds to L-rhamnose or D-galactose; and detecting the fluorescence level in the sample, wherein the presence of fluorescence indicating the presence of the cancer or tumor, wherein the cancer or tumor cell expresses an antigen comprising a carbohydrate capable of specifically binding to the SHA protein, the homologue of the SHA protein, or an SHA protein fragment or a homologue of the SHA protein fragment.

2. The method of claim 1, wherein the sample includes a biopsy sample, a tissue sample, a bronchoalveolar lavage sample, a blood sample, and a urine sample.

3. The method of claim 1, wherein the cancer is colon cancer, pancreatic ductal carcinoma, or pancreatic cancer.

4. The method of claim 1, wherein the antigen is a surface antigen comprising a carbohydrate containing D-galactose.

5. The method of claim 1, wherein the fusion protein specifically binds to a carbohydrate that contains or terminates in a monosaccharide or an oligosaccharide selected from the group consisting of β-Gal-; α-Rha-; Gal-α-1,3-Gal-β-1,3-GlcNAc-β-; Gal-α-1,3-Gal-β-1,4-Glc-β-; Gal-α-1,4-Gal-β-1,3-GlcNAc-β-; Gal-α-1,3-(Fuc-α-1,2)-Gal-β-; Gal-α-1,3-(Fuc-α-1,2)-Gal-β-1,4-Glc-β-; Gal-α-1,3-Gal-β-, Gal-α-1,4-Gal-β-1,4-Glc-β-; GalNAc-β-1,3-Gal-β-1,4-Glc-β-; and Gal-α-1,4-Gal-β-1,4-GlcNAc-β-.

6. The method of claim 1, wherein the fluorescent protein includes GFP and mCherry1.

* * * * *